United States Patent
Grabe et al.

(10) Patent No.: US 9,726,676 B2
(45) Date of Patent: Aug. 8, 2017

(54) MEANS AND METHODS FOR THE PREDICTION OF TREATMENT RESPONSE OF A CANCER PATIENT

(76) Inventors: Niels Grabe, Hirschberg (DE); Niels Halama, Heidelberg (DE); Dirk Jaeger, Heidelberg (DE); Inka Zoernig, Frankfurt am Main (DE)

(*) Notice: Subject to any disclaimer, the term of this patent is extended or adjusted under 35 U.S.C. 154(b) by 522 days.

(21) Appl. No.: 13/825,729

(22) PCT Filed: Sep. 20, 2011

(86) PCT No.: PCT/EP2011/004710
§ 371 (c)(1),
(2), (4) Date: Aug. 28, 2013

(87) PCT Pub. No.: WO2012/038068
PCT Pub. Date: Mar. 29, 2012

(65) Prior Publication Data
US 2013/0330325 A1    Dec. 12, 2013

(30) Foreign Application Priority Data
Sep. 24, 2010 (EP) .................... 10010537

(51) Int. Cl.
*G01N 33/68* (2006.01)
*G01N 33/50* (2006.01)
*G01N 33/574* (2006.01)

(52) U.S. Cl.
CPC ..... *G01N 33/6893* (2013.01); *G01N 33/5011* (2013.01); *G01N 33/5091* (2013.01); *G01N 33/574* (2013.01); *G01N 2333/7051* (2013.01); *G01N 2333/70517* (2013.01); *G01N 2333/96436* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,711,283 B1* | 3/2004 | Soenksen | G02B 21/002 382/128 |
| 2004/0004614 A1* | 1/2004 | Bacus | G06T 3/40 345/419 |
| 2005/0260646 A1 | 11/2005 | Baker | |
| 2007/0230755 A1* | 10/2007 | Maddison | G02B 21/367 382/128 |

FOREIGN PATENT DOCUMENTS

WO    WO 2007/045996    4/2007

OTHER PUBLICATIONS

Galon et al (Science, 2006, vol. 313, pp. 1960-1964).*
Hsu et al (Cancer Investigations, 2010, vol. 28, pp. 765-773).*
Wolf et al (The Laryngoscope, 2002, vol. 112, pp. 1351-1356).*
Galon et al (Supporting on-line material for Science, 2006, vol. 313, pp. 1960-1964) pp. 1-30.*
Halama et al (Analytical and Quantitative Cytology and Histology, 2010, vol. 32, pp. 333-340).*
Pachter, Journal of Neuropathology and Experimental Neurology, 2003, vol. 62, pp. 593-604.*
Halama, N., et. al., "The Localization and Density of Immune Cells in Primary Tumors of Human Metastatic Colorectal Cancer Shows an Association With Response to Chemotherapy," 2009, pp. 1-6, vol. 9.
Morris, M., et. al., "Tumor-Infiltrating Lymphocytes and Perforation in Colon Cancer Predict Positive Response to 5-Fluorouracil Chemotherapy," 2008, pp. 1413-1417, vol. 14.
Halama et al., "Hepatic metastases of colorectal cancer are rather homogeneous but differ from primary lesions in terms of immune cell infiltration," OncoImmunology, 2(4):e24116, 11 pages, (2013).
Halama et al., "Localization and Density of Immune Cells in the Invasive Margin of Human Colorectal Cancer Liver Metastases Are Prognostic for Response to Chemotherapy," Cancer Res; 71(17); 5670-5677, (2011).
WIPO Application No. PCT/EP2011/004710, International Search Report, mailed Mar. 29, 2012.
WIPO Application No. PCT/EP2011/004710, Written Opinion of the International Searching Authority, mailed Mar. 29, 2012.
WIPO Application No. PCT/EP2011/004710, International Preliminary Report on Patentability, issued Mar. 26, 2013.

* cited by examiner

Primary Examiner — Karen Canella
(74) Attorney, Agent, or Firm — Alston & Bird LLP

(57) ABSTRACT

The present invention relates to the field of treatment efficacy prediction in patients with malignant diseases. More precisely, this invention relates to the prediction of the efficacy of a treatment in cancer patients, based on the precise quantification of several biological markers that are related to the innate and adaptive immune response of said patient against said cancer.

13 Claims, 7 Drawing Sheets

MEANS AND METHODS FOR THE PREDICTION OF TREATMENT RESPONSE OF A CANCER PATIENT

CROSS-REFERENCE TO RELATED APPLICATIONS

This application is the U.S. National Stage of International Application No. PCT/EP2011/004710, filed Sep. 20, 2011, which designates the U.S. and was published by the International Bureau in English on Mar. 29, 2012, and which claims the benefit of European Patent Application No. 10010537.8, filed Sep. 24, 2010, all of which are hereby incorporated by reference in their entirety.

FIELD OF THE INVENTION

The present invention relates to the field of treatment efficacy prediction in patients with malignant diseases.

More precisely, this invention relates to the prediction of the efficacy of a treatment in cancer patients, based on the precise quantification of several biological markers that are related to the innate and adaptive immune response of said patient against said cancer.

BACKGROUND OF THE INVENTION

Advanced stages of cancer represent a challenging therapeutic medical problem with a poor prognosis for the patient. These patients often require multiple medical treatments and interventions and in most cases treatment is purely empirical. As treatment costs rise with novel therapies, the need for reliable diagnostic tools to guide treatment decisions is paramount. As cancer is the second leading cause of death in the western world and in aging societies cancer becomes more prevalent, vast amount of efforts and financial resources are being invested in the development of novel therapeutical and diagnostic approaches. However, the essential step for the multitude of available new therapies is the efficient selection of patients for adequate cancer therapy. Currently, most of the currently known markers of cancer therapy efficacy are poorly reliable.

Standard classification for malignant tumors relies on the TNM system. The TNM (for "Tumor-Node-Metastasis") classification system uses the size of the tumor, the presence or absence of tumor in regional lymph nodes, and the presence or absence of distant metastases, to assign a stage to the tumor (AJCC Cancer Staging Manual, Lippincott, 5thedition, pp. 171-180, 1997). Using this system, the assigned stage forms the basis for selection of appropriate therapy and also for prognostic purposes. Specifically, in colorectal cancers, the TNM system allows the distinction between (T) the degree of invasion of the intestinal wall, ranging from T0 to T4, (N) the degree of lymph node involvement, ranging from N0 to N3 and (M) the degree of metastasis, ranging from M0 to M1.

A meta-score for colorectal cancers is the Duke's classification. Duke's classification allows the distinction between at least four main tumor stages, respectively (A) tumor confined to the bowel wall, (B) tumor extending across the bowel wall, (C) involvement of regional nodes and (D) occurrence of distant metastases. A similar system is the staging system of the UICC, ranging from stage I (local tumor without metastases) to IV (tumor with distant organ metastases). These meta-scores are used to select patients for treatment options. UICC stage III patients usually receive chemotherapy after complete resection of the tumor tissue, while UICC stage IV usually receive palliative chemotherapy. It is still a controversy, whether UICC stage II patients require an adjuvant chemotherapy.

The above clinical classifications are useful in the clinical situation, but are completely imperfect in predicting the outcome of the intended therapy.

A similar situation can be found in other tumor entities. In breast cancer, expression of the protein HER2/neu by the tumor and other endocrine receptors is used to select patients for therapy strategies. Despite these selections, the variability in response to therapy is still big. Newer treatments with targeted drugs like monocolonal antibodies also give rise to some stratification of the patients. Modern chemotherapy regimens including monoclonal antibodies lead to objective response rates of around 50% in colorectal cancer patients, while almost half of the patients experience treatment related side effects without any clinical benefit. K-ras mutation is the only (negative) predictive marker for response to EGFR-targeting antibody treatment (Benvenuti et al. 2007, Cancer Res 67: 2643-2648) (Moroni, M et al. 2005, Lancet Oncol 6: 279-286). So far, no biomarkers are available that help to select patients that are likely to respond to chemotherapy.

Instead of conventional clinical staging, it has been proposed to use a large number of biological markers, including genes and proteins, that would be potentially useful for the diagnosis or the prognosis of a wide variety of cancers. Prognostic prediction and prediction of therapeutic efficacy are however not directly linked. Patients can have a response to a treatment but still have a shorter survival time then patients with no response to treatment (Farmer et al. 2009, Nat Med 15: 68-74).

It has not been proposed so far, that the presence of, or the expression level of, various biological markers of the host immune response in conjunction with the occurrence of a cancer at a given stage of cancer development was associated with the general response to treatment (i.e. treatment efficacy). For immunotherapeutic strategies, this association of a pre-existing immune response with a better therapeutic efficacy was assumed (see below). For chemotherapy, radiation therapy and other forms of drug intervention, this association has not been shown.

Nistico et al. (1999, Int. J. Cancer, Vol. 84: 598-603) assumed the existence of a spontaneous immune response against the erbB-2 oncogene product in HLA-A2-positive breast cancer patients. The impact of this immune response was thought to be dependent on tumor HLA-class-I molecule expression and on CD3+-T-lymphocyte localization, i.e. in intratumoral (IT) or peritumoral (PT) tissue. The authors reasoned, that these results could lead to the identification of new parameters that might be useful for defining more specific and more effective immunotherapeutic strategies against breast cancer.

A more elaborate approach was performed by Philips et al. (2004, British Journal of Surgery, Vol. 91: 469-475). They showed that tumour-infiltrating lymphocytes in colorectal cancer with microsatellite instability are activated and cytotoxic, by assaying both (i) the CD8/CD3 mRNA ratios and (ii) the CD3, CD4, CD8, cytokine IL-2Ra and Granzyme B protein production in the tumor tissue. There was however no significant correlation between mRNA copy numbers as T cell markers and immunohistochemical counts. Moreover there was no correlation with therapy response.

Maki et al. (2004, J. Gastroenterology and Hepatology, Vol. 19: 1348-1356) showed an impaired cellular immune system response in hepatocellular carcinoma-bearing patients. Decreased CD3[zeta] and CD28 protein expression by T cells was found in these patients, as well as an increased caspase-3 activity in CD28 down-modulated T cells. This suggests the occurrence of T cell apoptosis in HCC patients. Decreased expression of CD3[zeta] in T cells infiltrating cervical carcinoma was also reported by Grujil et al. (1999, British Journal of Cancer, Vol. 79: 1127-1132). These authors suggested that, in order for vaccination strategies to be successful, it might be essential to first identify and counteract mechanisms leading to this loss of CD3[zeta].

Ishigami et al. (2002, Cancer, Vol. 94 (5): 1437-1442) showed that reduced CD3-[zeta] expression is negatively correlated with lymph node involvement, depth of invasion, and clinical stage of gastric carcinoma. A reduced CD3-[zeta] expression correlates with a reduced 5-year survival rate of the patients, but only for patients which were diagnosed as "Stage IV" of gastric carcinoma. No information on treatment or association with treatment outcome is made.

An altered immune response in cancer patients was also found through the assessment of the expression of CD3, CD4, CD8 and Fas Ligand proteins on tumor-infiltrating lymphocytes (TILs) in head and neck cancer (Reichert et al. (2002, Clinical Cancer Research, Vol. 8: 3137-3145). This was also reported by Prado-Garcia et al. (2005, Lung Cancer, Vol. 47: 361-371), investigating the evasion mechanisms of lung adenocarcinoma by measuring the percentages of CD3+, CD4+ and CD8+ cells in peripheral blood and pleural effusion, and further CD27, CD28, CD45R0, CD45RA, granzyme A, Fas and perforin protein expression in the CD8+ T cell subsets. The characterization of these alterations that enable adenocarcinoma cells to inhibit CD8+ T cells in the initiation, growth and invasion processes of lung carcinoma, was proposed to allow the development of improved treatments for lung malignancies. Similar observations were made by Kuss et al. (2003, British Journal of Cancer, Vol. 88: 223-230)

Diederichsen et al. (2003, Cancer Immunol, Immunother., Vol. 52: 423-428) showed that colorectal patients with low CD4+/CD8+ ratios in TILs had a better clinical course, with significantly higher 5-year survival, independent of the Dukes stage and age.

Valmori et al. (2002, Cancer Research, Vol. 62:1743-1750) showed that the presence of a CD45RA+CCR7-CD8+ PBL T cell subset is associated with cytolytic activity in melanoma patients. These observations suggested an improved anti-tumor vaccination via the stimulation of such an effector immune response early in the course of the disease. The authors hypothesize, that such a response might be effective to eradicate minimal residual disease and prevent relapses.

Oshokiri et al. (2003, Journal of Surgical Oncology, Vol. 84: 224-228) reported a statistically significant association between the infiltration of cancer cell nests by CD8+ T cells and the survival in patients with extrahepatic bile duct carcinoma (EBDC). These authors showed that the level of CD8+ T cell infiltration correlated well with the conventional pTNM clinicopathological classification and that the infiltrate density was reliable for predicting the survival of patients with EBDC. Response to chemotherapy and association of the infiltrate density in this cancer entity was not investigated.

Menon et al. (2002, Lab Invest. 82, 1725-33) showed that the down-regulation of HLA-A expression correlates with a better prognosis in colorectal cancer patients. HLA molecules have a fundamental role in distinguishing "self versus" "not-self" (or "altered self") for the immune system. Furthermore Menon et al. (2004, Lab Invest. 84, 493-501) conducted a detailed immunohistochemical analysis to corroborate the association between immune system and prognosis in colorectal cancer.

Furthermore, Zhang et al. (2003, New England Journal of Medicine, Vol. 348(3) 203-213) showed, that the presence or absence of intratumoral T cells correlates with the clinical outcome of advanced ovarian carcinoma after debulking and adjuvant chemotherapy. They however did not associate the outcome with the administered chemotherapy and thus no conclusion on the relation between infiltrate density and chemotherapy outcome was stated. The results were obtained through immunostaining assays of tumor cryosections with monoclonal antibodies against CD3, CD4, CD8, CD83, CD45, CD45R0, CD19, CD57 and CD11c, as well as through flow cytometry of cells from fresh tumor samples using monoclonal antibodies against HLADR, CD3, CD4, CD8, CD16, CD19, CD45, IgG1 and IgG2a. These authors had detected the presence or absence of CD3+ tumor-infiltrating T cells within tumor-cell islets and in peritumoral stroma. These authors reported that patients whose tumors contained higher numbers of T cells had both a median duration of (i) progression-free survival and (ii) overall survival which was statistically higher than patients whose tumors did not contain T cells. These authors suggested to further validate the use of detection of intratumoral T cells in the classification and treatment of patients with ovarian carcinoma.

Galon et al. (2006, Science, vol. 313, 1960-1964) elegantly showed that the type, density, and location of immune cells within human colorectal tumors predicts clinical outcome in terms of overall survival and progression free survival. Again, immunohistochemistry was used to stain CD3, CD8, Granzyme B and CD45RO. The authors however did not differentiate the results with regards to the role of any therapy, especially radiation- or chemotherapy. Additional previous work however clearly had shown the role of the adaptive immune response in colorectal cancer. This was published by Pages et al. (2005, New England Journal of Medicine, vol. 353: 2654-2666).

All the above mentioned publications state the use of numerous biological markers of the immune response in the course of understanding the mechanisms of the immune response against various cancers. However, these prior works provide no data relating to a statistical significant relationship between (i) the presence of, or the expression level of, these biological markers and (ii) treatment efficacy for chemotherapy, radiation therapy or immunotherapeutic interventions.

Although the previous publications shows good correlation between (i) the presence of, or the level of, some biological markers of the immune response and (ii) the effect on overall or progression free survival of cancers, the results of most of these prior studies also show that the use of the said biological markers were viewed exclusively as a confirmation of a prognostic cancer staging with conventional clinicopathological staging methods, or as an additional information to the said conventional cancer staging methods. For example, the biological marker used by Ishigami et al. (2002, above) was found to be useable exclusively with gastric carcinoma-bearing patients who were already diagnosed as "Stage IV" of the disease. Similarly, Zhang et al. (2003, above) concluded that prospective studies were needed to validate detection of intratumoral (CD3+) T cells in the classification and treatment of patients with ovarian carcinoma. Similarly, Diederichsen et al. (2003, above) disclosed the CD4+/CD8+ ratio as a biological marker having a survival prognostic value in colorectal cancer. However, these authors did not suggest that the said biological marker might be sufficient to influence a therapeutic decision or to predict therapeutic efficacy.

There is thus no report of reliable methods of cancer prognosis prediction that would make use exclusively of biological markers of the immune response from the host to estimate the efficacy of chemotherapy. Neither is there a reliable method for the prediction of treatment outcome in cancer patients.

Morris et al. (2008, Clin Cancer Res., vol 14: 1413-1417) used an analysis in the adjuvant treatment setting to state that tumor-infiltrating lymphocytes and perforation in colon cancer predict positive response to 5-fluorouracil chemotherapy. This however cannot be concluded from their data, because they only analysed the adjuvant treatment situation, so it remains unclear, how the adaptive immune response influences chemotherapy outcome in the light of only short term chemotherapy and long periods of follow-up.

Farmer et al. (2009, Nature Medicine, Vol 15: 68-74) identified a stroma-related gene signature that predicts resistance to neoadjuvant chemotherapy in breast cancer. They however did not identify immunological parameters for this prediction. In Baker et al. (U.S. Pat. No. 7,871,769, approved Apr. 19, 2011) the RNA expression levels of a set of genes is used to calculate a score to predict the response to chemotherapy but it does not measure the immune status of the patient.

Further, there is, today, no reliable marker available that would allow the prediction of the treatment outcome in all investigated cancer entities. This is also true for immunotherapeutic approaches, where also no good predictor of treatment outcome is available.

Notably, the availability of improved prediction methods would allow a better selection of patients for appropriate therapeutic treatments, especially in the situation of palliative treatment. Other important therapeutic interventions that could be improved by a better patient selection are immunotherapies. Immunotherapies are all therapies that either directly or indirectly modify the immune response or the immune system of a patient. For numerous cancers including colorectal cancers, the selection of an appropriate therapeutical treatment is purely empirical today. 55% of colorectal cancer patients undergoing palliative chemotherapy treatment have a response to chemotherapy. The rest of these patients only experiences side effects of the therapy. The genomic mutation status for KRAS is the only predictive marker for an antibody-based treatment regimen, as reported by Moroni et al. (2005, Lancet Oncol, vol 6: 279-86). Thus, the guided treatment would lead to better outcomes by reduction of toxicity and reduction of unnecessary side effects.

SUMMARY OF THE INVENTION

Thus, in view of the state of the art, there is a need for means and methods to predict chemotherapy response in cancer patients, including colorectal cancers, that are more accurate and more reliable than the presently available methods, which are essentially, if not exclusively, clinicopathological staging methods or genomic data. Accordingly, the technical problem of the present invention is therefore to comply with the need set out in the prior art.

The present invention addresses this need and thus provides as a solution to the technical problem embodiments pertaining to means and methods for predicting a patient's response to cancer therapy, in particular chemotherapy and immunotherapy. These embodiments are reflected in the claims and described in detail herein.

In particular, the present invention provides a novel method for the prediction of treatment efficacy in a cancer patient. More specifically, the present invention provides means and methods for predicting a potential response of a cancer patient to cancer therapy, in particular immunotherapy and chemotherapy. This novel method is based on the detection and/or the quantification, at the tumor site, of one or more biological markers indicative of the presence of, or alternatively of the level of, the (presence of) adaptive and innate immune (cells or) response of said patient against said cancer.

More specifically, it has surprisingly been found that a precise determination of an in situ immune response of a patient to cancers, and especially to colorectal cancers, can be used as a parameter for predicting the subsequent clinical response to treatment, regardless of the extent of local tumor invasion and spread to regional lymph nodes or the administered treatment regimen (e.g., chemotherapy, radiation, etc.). Such a treatment may also comprise adoptive immunotherapy in which an individual's own white blood cells are coupled with a naturally produced growth factor to enhance their cancer-fighting capacity.

In detail, in their investigations, the present inventors found that the immunohistochemical quantification of immune cells in a tumor tissue section, in particular, by whole slide imaging technology by the use of at least one biological marker which is indicative of the immune response of a patient against cancer is potentially predictive of the patient's response to chemotherapy. Specifically, a comparison of the quantification value with a predetermined reference value of said biological marker can potentially indicate as to whether a patient may or may not respond to chemotherapy.

Indeed, a value higher than the reference value may indicate that the patient would respond to chemotherapy. However, a value lower than the reference value may indicate that the patient would not respond to chemotherapy or immunotherapy.

Likewise, for some biological markers a value lower than the reference value may indicate that the patient would respond to immunotherapy or chemotherapy. However, for some biological markers a value higher than the reference value may indicate that the patient would not respond to immunotherapy or chemotherapy.

In more detail, the present inventors found that a scoring system for primary or metastatic lesions of human colorectal cancer using whole tissue section immunohistochemical analysis as a tool to predict treatment response in these patients. Accordingly, they developed a scoring system to differentiate between patients with high or low TIL densities and to separate patients who responded to chemotherapy from those who did not respond to chemotherapy. An independent set of patients ("validation set") was used to validate the scoring system with respect to response prediction. Recursive partitioning analyses by conditional inference trees of the observed TIL densities (CD3, CD8, Granzyme B) of the 22 metastatic lesions in the training set revealed the following prediction rule: patients having a CD3 cell count above 600 cells/mm$^2$ are predicted to respond to therapy (P<0.001). Since one non-responder was misclassified as responder the rule was extended using the patient's CD8 and Granzyme B data. The finally derived rule required a CD3 cell count above about 600/mm$^2$ and either a CD8 density of higher than about 200/mm² or a Granzyme B density of higher than about 30/mm² to predict response to treatment.

Accordingly, aspects of the present invention are

1. A method for predicting whether a cancer patient is responsive to treatment with cancer therapy, preferably chemotherapy or immunotherapy, comprising determining in a tumor sample from said patient the number of cells which are CD3-positive and CD8-positive and/or Granzyme B-positive, wherein a number of CD3-positive and CD8-positive and/or Granzyme B-positive cells, that is above a predetermined number of said cells, which is indicative for patients not responding to chemotherapy, is indicative that said patient is responsive to cancer therapy, preferably chemotherapy or immunotherapy.
2. The method of item 1, wherein the determination of the number of cells is conducted by using whole slide imaging technology.
3. The method of item 1 or 2, wherein the number of cells is determined as density of cells per square millimeter (mm²).
4. The method of any one of items 1 to 3, wherein the number of cells is determined with immunohistochemistry and/or with immunofluorescence.
5. The method of any one of items 1 to 4, wherein the cells are detected by a labelled antibody or a labelled nucleic acid probe.
6. The method of any one of items 1 to 5, wherein a number of at least about 600 CD3-positive cells/mm² and at least about 200 CD8-positive cells/mm² and/or at least about 30 Granzyme B-positive cells/mm² is indicative that said patient is responsive to cancer therapy, preferably chemotherapy or immunotherapy.
7. The method of any one of items 1 to 6, wherein said cancer is metastasizing cancer.
8. The method of any one of items 1 to 7, wherein said cancer is colorectal cancer.
9. The method of any one of items 1 to 8, wherein said tumor sample is a sample from a primary tumor or a metastasis.
10. The method of item 9, wherein said tumor sample is a tumor tissue section or a blood sample (or a derivative of a blood sample).
11. The method of item 9 or 10, wherein said tumor sample comprises the center of the tumor and/or tissue directly surrounding the tumor.
12. The method of item 11, wherein said tumor sample comprises
    (i) lymphoid islets in proximity to the tumor;
    (ii) lymph nodes located in proximity of the tumor; and/or
    (iii) adjacent normal tissue or blood from the periphery.
13. The method of any one of items 1 to 12, wherein said cells are immune cells
14. The method of item 13, wherein said T cells are tumor infiltrating lymphocytes (TILs).
15. The method of item 14, wherein said immune cells are T cells, macrophages, dendritic cells, fibroblasts, NK cells, NKT cells or NK-DC cells or any other immunologically active cell.
16. The method of any one of items 1 to 15 further comprising determining the level of at least one further biological marker being indicative of an immune response of the patient against the cancer, wherein a level that is above a predetermined level, which is indicative for patients not responding to cancer therapy, preferably chemotherapy or immunotherapy, is indicative that said patient is responsive to cancer therapy, preferably chemotherapy or immunotherapy.
17. The method of item 16, wherein said biological marker is a protein which is indicative of an immune response, wherein a level of the protein that is above a predetermined level, which is indicative for patients not responding to cancer therapy, preferably chemotherapy or immunotherapy, is indicative that said patient is responsive to cancer therapy, preferably chemotherapy or immunotherapy.
18. The method of item 16 or 17, wherein said biological marker is one or more selected from the group consisting of
    (a) immunological markers;
    (b) biological markers of Th1/Th2 cells;
    (c) biological markers of the Interferon family;
    (d) biological markers of the Common gamma Chain Receptor Family;
    (e) biological markers of the CX3C Chemokines and Receptors;
    (f) biological markers of CXC Chemokines and Receptors;
    (g) biological markers of CC Chemokines and Receptors;
    (h) biological markers of CC Chemokine Inhibitors;
    (i) biological markers of C Chemokines & Receptors Lymphotactin (also known as SCM-1 alpha) and SCM-1 beta, C Chemokine Ligands, XCL1/Lymphotactin, C Chemokine Receptors, XCR1;
    (j) biological markers of other Interleukins;
    (k) stem cell markers and molecules secreted by stem cells or leading to activation or mobilization of stem cells; and
    (l) biological markers of growth factors, their receptors and correlated downstream-signalling molecules.
19. The method of item 18, wherein a level of interferon gamma of above 1000 ng/ml is indicative for a response to cancer therapy.
20. The method of item 18, wherein a ratio interferon gamma to RANTES higher than 1 is indicative for a response to cancer therapy.
21. The method of item 18, wherein the biological marker is MIF, IL-1ra and/or CCL2 or a combination thereof.
22. The method of any one of items 1 to 18, wherein a concentration of VEGF and/or IL-8 in a sample from a patient that is higher in comparison to a patient not suffering from cancer and/or a concentration of interferon gamma, MIG, IP-10 and/or Fractalkine in a sample from a patient that is lower in comparison to a patient not suffering from cancer, is indicative that said patient is not responsive to cancer therapy, preferably chemotherapy or immunotherapy.
23. One or more chemotherapeutic agents for use in the treatment of a cancer patient, said cancer patient is having a tumor characterized by the infiltration of at least about 600 CD3-positive cells/mm² and at least about 300 CD8-positive cells/mm² and/or at least about 30 Granzyme B-positive cells/mm² comprising administering to said patient one or more therapeutically effective chemotherapeutic agents.
24. A method of treating a cancer patient, said cancer patient is having a tumor characterized by the infiltration of at least about 600 CD3-positive cells/mm² and at least about 300 CD8-positive cells/mm² and/or at least about 30 Granzyme B-positive cells/mm² comprising administering to said patient a therapeutically effective chemotherapy.
25. A method of screening for a therapeutically effective chemotherapeutic agent for a cancer patient comprising the following steps:

(a) providing tumor cells from a tumor sample of said patient, wherein said tumor sample is characterized by the infiltration of at least about 600 CD3-positive cells/mm² and at least about 300 CD8-positive cells/mm² and/or at least about 30 Granzyme B-positive cells/mm²;
(b) contacting the tumor cells with one or more chemotherapeutic agents; and
(c) evaluating whether said one or more chemotherapeutic agents affects the tumor cells.

26. A method of stratifying cancer patients that are responsive to treatment with cancer therapy, preferably chemotherapy or immunotherapy, comprising determining the number of immune cells that infiltrate a tumor of a cancer patient, wherein a number of at least about 600 CD3-positive cells/mm² and at least about 300 CD8-positive cells/mm² and/or at least about 30 Granzyme B-positive cells/mm² indicates that the cancer patient is responsive to cancer therapy, preferably chemotherapy or immunotherapy.

27. The use of item 23 or the method of any one of items 24 to 26, wherein said cancer patient was identified with the method as described in item 26.

28. The use of item 23 or the method of any one of items 24 to 26, wherein said cancer patient was identified prior to and/or during treatment with chemotherapy.

29. The use of item 23 or the method of any one of items 24 to 26, wherein said cancer is colorectal cancer.

30. The use of item 23 or the method of item 29, wherein said chemotherapeutic agent is one or more selected from the group consisting of UFT, Capecitabine, CPT-II, Oxaliplatin, 5FU, 5FU continuous infusion, Paclitaxel, Docetaxel, Cyclophosphamide, Methotrexate, Doxorubicin, Navelbine (iv and oral), Epirubicin, Mitoxantrone, Raloxifen, Cisplatin, Mitomycin, Carboplatinum, Gemcitabine, Etoposide and Topotecan.

31. A pharmaceutical package comprising one or more chemotherapeutic agents, and
(a) instructions and/or an imprint indicating that said one or more chemotherapeutic agents is to be used for the treatment of a patient who suffers from cancer which is characterized by the infiltration of at least about 600 CD3-positive cells/mm² and at least about 300 CD8-positive cells/mm² and/or at least about 30 Granzyme B-positive cells/mm²; and/or
(b) instructions and/or an imprint indicting that said patient is to be stratified by the method described in item 26; and/or
(c) means to carry out a method as described in any one of the preceding items.

32. A method for the prediction of treatment response of malignant disease in a sample of a patient, comprising at least one of the following steps:
(a) quantification of cells in the sample with at least one biological marker being indicative of the immune response of the patient against the disease, a result of which is outlined in a quantification value;
(b) comparing the quantification value of step a) with a predetermined reference value for the said biological marker correlated with a specific treatment outcome of said disease;
(c) quantification of at least one protein level being indicative of the immune response in correlation to the identified immune cell quantities of step a), a result of which is outlined in a quantification value;
(d) comparing the quantification value of step (c) with a predetermined reference value for the said protein correlated with a specific treatment outcome of said disease.

33. The method of item 32, wherein the biological marker is a cell, a part of a cell, a peptide, a polypeptide or a nucleotide sequence.

34. The method of item 33, wherein the cell is an immune cell.

35. The method of any one of items 32 to 34, wherein the biological marker is expressed from a cell or is part of a cell from the immune system or from malignant tissue causing the disease or is expressed from a cell associated with the malignant tissue or is expressed from a cell of normal tissue adjacent to the malignant tissue.

36. The method of any one of items 32 to 35, wherein the said at least one biological marker is quantified with at least one in situ immunohistochemical method or in combination with staining of fluorescently labelled probes.

37. The method of any one of items 32 to 36, wherein the said at least one biological marker is detected by a labelled antibody or a labelled nucleic acid probe.

38. The method of any one of items 32 to 37, wherein the said at least one biological marker consists of the number of density of cells from the immune system contained in at least one tissue according to item 35 and the concentration of a protein of interest in the malignant tissue.

39. The method of any one of items 32 to 37, wherein the said at least one biological marker consists of the quantification value of a protein produced by the immune cell or by a cell according to item 35 associated with tissue present at the malignant tissue causing the disease.

40. The method of any one of items 32 to 39 using whole slide imaging technology.

41. The method of any one of items 32 to 40, wherein the said at least one biomarker is quantified in a tumor tissue sample selected from the group consisting of:
(a) a global primary tumor,
(b) a complete tumor tissue section comprising the center of the tumor and tissue directly surrounding the tumor in conjunction with at least
(i) lymphoid islets in proximity to the tumor;
(ii) lymph nodes located in proximity of the tumor;
(iii) tumor tissue sample collected prior to surgery or during treatment;
(iv) tissue sample from a distant metastasis encompassing metastatic lesion;
(v) adjacent normal tissue or blood sample (peripheral blood).

42. The method of any one of items 32 to 41, wherein the said at least one biological marker is selected from at least one group consisting of:
(a) Various biological and immunological markers;
(b) Biological markers of Th1/Th2 cells;
(c) Biological markers of the Interferon family;
(d) Biological markers of the Common gamma Chain Receptor Family;
(e) Biological markers of the CX3C Chemokines and Receptors;
(f) Biological markers of CXC Chemokines and Receptors;
(g) Biological markers of CC Chemokines and Receptors;
(h) Biological markers of CC Chemokine Inhibitors;
(i) Biological markers of C Chemokines & Receptors Lymphotactin (also known as SCM-1 alpha) and SCM-1 beta, C Chemokine Ligands, XCLI/Lymphotactin, C Chemokine Receptors, XCR1;
(j) Biological markers of other Interleukins;
(k) Stem cell markers and molecules secreted by stem cells or leading to activation or mobilization of stem cells;
(l) Biological markers of growth factors, their receptors and correlated downstream-signalling molecules.

43. The method according to items 40 to 42, wherein protein concentration of at least one distinct biological marker is quantified in the whole tissue sample or given regions within or near the tumor.

44. The method according to any one of items 32 to 43, wherein the said at least one biological marker indicative of the immune response of said patient against tissue causing malignant disease is expressed by an immunologically active cell such as a B lymphocyte-cell, T lymphocyte cell, dendritic cell, NK cell, NKT cell, NK-DC cell, myelo-derived suppressor cell, mast cell, macrophages, fibroblasts or from colorectal cancer cell, breast cancer cell or from endothelial cell, fibroblast, myeloid stem cell or precursor cell associated with the cell from malignant tissue.

45. The method according to any one of items 32 to 44, wherein fluorescently labelled antibodies and conventional antibodies of several targets are simultaneous evaluated in one tissue sample by combining fluorescence microscopy with bright-field microscopy, mass spectrometry, Enzyme-linked Immunosorbent Assay (ELISA) or other verification procedure on one tissue slide.

46. A kit for the response to treatment prediction of malignant disease in a sample of a patient comprising means for quantifying at least one biological marker indicative of the immune response of said patient against said disease.

47. The kit of item 46, wherein the malignant disease is cancer.

48. The kit of item 47, wherein the cancer is breast cancer, prostate cancer, liver cancer, lung cancer or colorectal cancer and other tumor entities.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

As described herein, "preferred embodiment" means "preferred embodiment of the present invention". Likewise, as described herein, "various embodiments" and "another embodiment" means "various embodiments of the present invention" and "another embodiment of the present invention", respectively.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

DETAILED DESCRIPTION OF THE INVENTION

The present inventors found that there is a highly significant relationship (e.g. low P values) between (i) biological markers (biomarkers) including the type, density, and location of immune cells within tumors as detected on whole slide tissue sections and (ii) the clinical outcome of treatment, encompassing PFS and RT. This highly significant correlation has been found by the use of biological markers of the immune response, either based on (i) immunochemistry assays on whole slide tissue sections or (ii) protein (cytokine and chemokine) expression analysis (based on prior imaging analyses encompassing whole slide tissue section analysis, mRNA expression).

Specifically, as mentioned above, the present inventors have found that there is a significant correlation between the density of immune cells, in particular T cells, more particularly tumor infiltrating T cells (TILs), at the tumor site and response to therapy, in particular response to chemotherapy. In fact, it was shown that a lasting response to chemotherapy is highly correlated with a high density of the biomarkers CD3+ cells, CD8+ cells, FOXP3 or Granzyme-B+ cells at the site of the tumor, either in the central part of the tumor or in the invasive margin thereof.

Furthermore, it has been found that the determination of the presence of high densities of CD3+ cells, CD8+ cells, CD45RO+ cells or Granzyme-B+ cells at the site of the tumor is highly correlated with longer periods of response to chemotherapy. Additional biomarkers include FOXP3, CD20, NKp46, CD31, Chymase, Tryptase, PD-1, PD-L1, TIM3, CCL5, MIG, IP10, CD54, CD163 and/or CD47.

Also, it was found that cytokines and chemokines analyzed at the primary tumor site and in metastases are useful biomarkers for prognosis and treatment response. These include, but are not limited to interferon gamma, IL-1b, IL-1ra, IL-2, IL-4, IL-5, IL-6, IL-7, IL-8, IL-9, IL-10, IL-12, IL-13, IL-15, IL-17, Eotaxin, FGF basic, G-CSF, GM-CSF, IFN-g, IP-10, MCP-1, MIP-1a, MIP-1b, PDGF-bb, RANTES, TNF-a, VEGF, CTACK, GRO-a, HGF, sICAM-1, IFN-a2, sCD25, IL-3, IL-16, IL-18, LIF, MCP-3, M-CSF, MIF, MIG, b-NGF, SCF, SCGF-b, SDF-1a, TNF-b, TRAIL, sVCAM-1, IL-1a, Angiopoietin-1, Angiopoetin-2, ALDH1, ABCG2.

More specifically, the level of Interferon gamma were also found to be predictive for treatment response. Similarly, the ratio of Interferon gamma to RANTES is also of importance: an amount of Interferon gamma higher than RANTES is a good predictor for treatment response. The level of the amount necessary for a good treatment response varies between cancer entities but in some embodiments of the invention the level needs to be higher than 1000 ng/ml.

In addition, it has been shown that the related immune cell infiltrates are associated with a certain type of cytokine and chemokine profile within the tissue. The specific profile was correlated to the infiltrate density and type. The required tumor tissue for this analysis is small and therefore provides an elegant basis for minimal-invasive diagnostics, sparing massive clinical interventions.

As mentioned above, it has surprisingly been found that a precise determination of an in situ immune response of a patient to malignant cancers, and especially to colorectal cancers, can be used as parameter for predicting the subsequent clinical response to treatment, regardless of the extent of local tumor invasion and spread to regional lymph nodes or the administered treatment regimen (e.g., chemotherapy, radiation, etc.).

The statistically highly significant correlation between (i) the level of the immune response (or presence of specific immune cells) from a patient at the tumor site and (ii) the treatment efficacy is all the more surprising, because in accordance with prior art knowledge, the presence of infiltrating immune cells in mammal cancers was associated with highly variable outcomes and a relation to treatment was not shown.

The highly significant correlation that was surprisingly found by the present inventors allows an easy determination of the efficacy of a given treatment in a cancer patient.

As it will be detailed further herein, when determining the statistical correlation between (i) the presence of, or the level of, one or more biological markers of the immune response, as disclosed in the present application and (ii) the actual treatment efficacy of cancer in patients, encompassing progression-free survival (PFS) and response to therapy (RT), significant P values were obtained according to the invention.

Either single values for the biomarkers of the present invention can be used for the prediction or patterns of combined markers. The patterns may consist of different marker values that highlight the relation of pro-inflammatory or anti-inflammatory cells or proteins. Specific patterns therefore consist of specific constellations i.e. relations of these markers to each other that are typically found in a given clinical situation. This can, for example, be based on cell densities or marker intensities.

By analysis of biological markers of the immune response by immunohistochemical whole slide imaging analysis, either (i) in the center of the tumor (CT), (ii) in the cellular environment surrounding the tumor, which may also be termed the "invasive margin" (IM) or (iii) in both CT and IM, a number of significant combinations of markers were also found by the present inventors. Highest statistical correlation for individual patient values were found when the biological markers were quantified in the invasive margin (IM).

Further to the afore-mentioned findings, the present inventors have observed a significant improvement of fluorescent labelling ("immunofluorescence"). In particular, the present inventors combined the technology of immunofluorescence with conventional immunohistochemistry. Accordingly, the tissue slide is incubated with a fluorescently labelled antibody and is subsequent subject to standard immunohistochemical staining techniques. Following that, the slide is first scanned with a fluorescence scanner followed by conventional brightfield. The resulting images are then overlayed by a software program. This analysis provides a precise quantification of the biomarkers applied in the means and methods of the present invention.

In addition, in view of the fact that the distinct quantification of biomarkers in given regions is based on laser capture microdissection, the precise quantification of protein levels can be correlated to the density of immune cells. That high spatial resolution is therefore an important step in the analysis of the tumor sample.

Generally, this above mentioned procedure allows to measure simultaneously different fluorescently labelled target structures while preserving the morphology as seen in conventional immunohistochemistry. Indeed, it has been found according to the invention that the type, the density, and the location of immune cells in cancer patients, as assayed with this novel procedure yields a comprehensive predictive signature that is superior and independent of those currently available.

It has also been found that the detection of a strong immune response at the tumor site was a reliable marker for a plurality of cancers, like colon cancers as well as rectum cancers. Accordingly, the methods of prediction of the present invention are particularly suited for the predicting as to whether a cancer patient suffering from colon cancer and/or rectum cancer may respond to cancer therapy, in particular chemotherapy.

The publication by Denkert et al. 2009 J. Clin. Oncol. (28); 105-113 suggested a relation between the lymphocyte density in breast cancer patients as determined by tissue microarrays and the outcome of neoadjuvant chemotherapy. They however failed to show a predictive process for the individual patient, instead they had to analyze large cohorts of patients to estimate an association.

Our own work by Halama et al. (2010) Anal Quant Cytol Histol. 2010 32:333-340 has shown that the evaluation of only small regions of a given tumor, e.g. based on tissue microarrays, is not sufficient to make (prognostic) predictions due to the heterogeneity of immune cells or other markers in cancer samples. This clearly limits the observations by Denkert et al., as they do not have evaluated the tumor heterogeneity before using tissue microarrays and therefore cannot use their method for individual patients.

Therefore, it is important, as described herein, to perform a whole slide/whole tissue section analysis for the analysis of biomarkers or use this whole slide analysis for a cytokine/chemokine or protein profiling. Only this combined approach allows the reliable quantification of biomarkers. Thus it has been shown for the first time according to the invention that the quantification of the said biomarkers based on whole tissue sections allows the precise prediction of treatment response or time to progression under treatment in cancer patients.

Indeed, although various prior art works had pointed out the possible relevance of marker(s) of the immune response for cancer prognosis, these prior works contained only data that might be used for the assessment of the prognosis and not the response to treatment. Conventional cancer staging methods do not provide a means to predict treatment response. Thus, no prior art works disclosed nor suggested any reliable or reproducible in vitro cancer treatment prediction method that would be based exclusively on the measurement of one or more biological markers indicative of the immune response of the cancer-bearing patients.

Therefore performing the prediction with the methods of the present invention, will help identify those patients that will most likely not respond to treatment. Patients could therefore receive a suitable treatment option based on the method of invention. On the other hand, the method described likely identifies patients that may benefit from (adjuvant) therapy, including immunotherapy.

The above being said, the method of invention is not limited to patients with incurable disease, but instead can also be applied to patients who underwent curative treatment. E.g. in colorectal cancer, stage III patients usually receive adjuvant treatment, whereas the majority of these patients only experience side effects without a clinical prognostic benefit.

In essence, it has been found that the detection of a biomarker, in particular a certain type of immune response (either by cellular quantification or cytokine/chemokine quantification) at the tumor site is significantly correlated with a response to treatment (specifically chemotherapy or immunotherapy treatment) and better progression free survival under treatment. A particular preferred biomarker is CD3, CD8 and/or Granzyme B. More particularly, a cell number of at least 600 CD3-positive cells/mm$^2$, of at least 200 CD-8 positive cells/mm$^2$ and/or of at least 30 Granzyme B-positive cells/mm$^2$ was found to be indicative as to whether a cancer patient may respond favourably to cancer therapy, in particular chemotherapy.

Summarizing, the present inventors have found a significant a correlation between
- biomarkers, in particular the cell density of specific types of cells of the immune system, as assayed in an immunohistochemical assay (with conventional or with the specific novel process described above) using a single or a combined set of biological markers, and
- a progression free survival (under therapy) or response to therapy, in particular chemotherapy, with P values as low as P<0.001,
Preferably, the biomarkers are assayed on a complete tissue section (encompassing both the centre of the tumor and the invasive margin) by applying a combination of immunofluorescence and conventional immunohistochemistry.

Accordingly, in a first aspect, the present invention provides an in vitro method for the prediction of treatment response of a cancer patient, which method comprises the following steps:
a) quantifying, in a tumor tissue sample from said patient, at least one biological marker indicative of the status of the immune response (either by cellular quantification or cytokine/chemokine profiling) of said patient against cancer; and
b) comparing the value obtained at step a) for said at least one biological marker with a predetermined reference value for the same biological marker; which predetermined reference value is correlated with a specific outcome or progression free survival under treatment of said cancer.

In some preferred embodiments, step a) is performed by immunohistochemical quantification of immune cells in tumor tissue by whole slide imaging technology in a tumor tissue sample from said patient.
In other preferred embodiments, said at least one biological marker is indicative of the status (or activation) of the immune response of said patient against cancer.

In addition or in the alternative to steps a) and b) of the above method, prediction of treatment response of a cancer patient can be achieved as follows:
c) quantification of at least one cytokine and/or chemokine protein level indicative of the immune response in correlation to the above identified immune cell quantities; and
d) comparison of the values obtained in step c) for said at least one biological marker (cytokine or chemokine) with a predetermined reference value for the same biological marker; the predetermined reference value was identified to be correlated with a specific treatment outcome of said cancer. Step c) and d) are not necessary for all cancer entities.

In some preferred embodiments of the method, step a) consists of quantifying one or more biological markers by immunochemical techniques on complete tissue sections and especially both (i) in the center of the tumor (CT) and (ii) in the invasive margin (IM), whereas for each region a differentiation between stromal and epithelial compartments can be made.

In some other preferred embodiments of the method, step c) and d) are not necessary for all cancer entities, depending of the specifics of a given tumor tissue type.

The in vitro prediction method for the treatment outcome of cancer patients of the present invention may further comprise a step c) wherein the prediction result per se is provided.

Preferably, when the first step consists of the quantification analysis of one or more biomarkers with an immunohistochemical technique, i.e. one or more pertinent biological markers, then the quantification of the protein expression (e.g. cytokines or chemokines) is performed from the identified tumor tissue section.

Preferably, when the first step consists of the assessment of specific immune cell densities by a immunohistochemical assay for one or more cell-expressed biological makers, then the quantification is performed on the complete tissue section (whole slide analysis) and incorporates at least two distinct tumor tissue samples, among the tumor tissue samples labelled (a) to (b) and (i) to (iv) above. Most preferably, according to this embodiment, the quantification of the said one or more biological markers is performed differentially for the centre of the tumor (CT) and the invasive margin (IM).

As intended herein, the "immune response" encompasses the presence or the activity, including the activation level, of cells from the immune system and signalling molecules related to the immune system of the host cancer patient locally at the tumor site or generally, e.g. in the serum.

As intended herein, the expression "immune response of said patient against said tumor" encompasses any form of immune response of said patient through direct or indirect, or both, action towards said cancer.

The immune response means the immune response of the host cancer patient in reaction to the tumor and encompasses the presence of, the number of, or alternatively the activity of, cells and related signalling molecules involved in the immune response of the host which includes: all cytokines, chemokines, growth factors, stem cell growth factors, etc.

The immune response encompasses a multitude of different cellular subtypes as well as an enormous number of signalling molecules (cytokines, chemokines, other signalling molecules). As used herein, the T lymphocytes encompass T helper lymphocytes, including Th1 and Th2 T helper lymphocytes cell subsets, but also T cytotoxic lymphocytes. Besides the T cell lineage, also the B cell lineage, the natural killer cells, macrophages, dendritic cells, myelo-derived suppressor cells, lytic dendritic cells, fibroblasts, endothelial cells, etc.

The "status" of the immune response encompasses (i) the existence and quantity of a specific immune cell population or cytokine/chemokine level in response to cancer at the tumor site and the surrounding tissue.

Adaptive and Innate Immunity

In comparison to innate immunity, acquired (adaptive) immunity develops when the body is exposed to various antigens and builds a defense that is specific to that antigen.

Innate immunity relates to macrophages, natural killer cells and other acellular components (e.g. complement system). All these cells can react to alien antigens without prior activation or contact to that antigen. Innate and adaptive immunity are intertwined and influence each other profoundly.

The adaptive immune response is antigen-specific and may take days or longer to develop. Cell types with critical roles in adaptive immunity are antigen-presenting cells including macrophages and dendritic cells. These cells process foreign antigen and present that antigen to effector cells like T cells. Antigen-dependent stimulation of T cell subtypes, B cell activation and antibody production, and the activation of macrophages and NK cells all play important roles in adaptive immunity. The adaptive immune response also includes the development of immunological memory, a process that continues to develop throughout life and enhances future responses to a given antigen.

Lymphocytes, a special type of white blood cell, contain two major groups, B and T lymphocytes. These cells are key players in acquired immune responses. B lymphocytes (also called B cells) can differentiate to cells that produce antibodies. Antibodies are specific molecules that attach to a specific antigen and make it easier for the phagocytes to destroy the antigen or the cell with the antigen on the surface. T lymphocytes (T cells) and especially cytolytic T cells attack antigens directly, and provide control of the immune response. B cells and T cells develop that are specific for one antigen type. When the immune system is exposed to a different antigen, different B cells and T cells are formed.

As lymphocytes develop, they become tolerant to "self" antigens. "Self" means that they can recognize the body's own tissues as distinctive from tissues and particles not found in the body. Once B cells and T cells are formed, a few of those cells will differentiate and function as "memory" for the immune system. This forms the basis for the immune system to respond faster and more efficiently to already encountered antigens. This process of rejection of a already recognized foreign antigen is called "immunity". Cancer immunity therefore indicates that the host is able to counter malignant cells. However, malignant cells can have a multitude of different antigens on the surface and therefore it is possible that malignant cells arise that are not recognized by the immune system.

The innate immune response is based on cells that are able to detect foreign antigens without prior sensitization. This means that these cells can detect infected or malignant cells and efficiently kill these cells. There is an intricate interplay between the cells of the innate and the adaptive immune response. The precise network and interplay between these cells is unknown. Other cells like fibroblasts or endothelial cells are involved indirectly as they activate or inhibit immune reactions. Specialized cells like regulatory T cells or myelo-derived suppressor cells (MDSCs) inhibit the immune reaction. The latter cells usually have the function to prevent auto-reactivity or to quench immune reactions following a successful defense of an infection.

Signalling molecules involved in this process are cytokines and chemokines, e.g. interleukins. These molecules regulate activation or inactivation, migration and processing of danger signals within the tissue and control the interplay of immune cells. Therefore a broad range of specialized cytokines and chemokines are involved in the precise orchestration of immune responses. These molecules have differential functions on cells of the innate and the adaptive immune response.

A subset of immune cells are the cytotoxic T cells. Cytotoxic T cells recognize infected or malignant cells by using T-cell receptors to probe the surface of other cells. If they recognize an infected cell, they release granzymes to signal that cell to become apoptotic ("commit suicide"), thus killing that cell. A cytotoxic T cell is a T cell which has on its surface antigen receptors that can bind to fragments of antigens displayed by the class I MHC molecules of virus infected somatic cells and tumor cells. Activation by a MHC-antigen complex, leads to the release the protein perforin, which forms pores in the target cell's plasma membrane, thereby killing the target cell. Another molecule involved is granzyme, a serine protease, that can enter target cells via the perforin-formed pore and induce apoptosis (cell death). Usually, cytotoxic T cells have on the cell surface the protein CD8, which interacts with class I MHC molecules. This interaction binds the T cell and the target cell together for specific activation.

Another important subset of T cells are helper T cells (TH cells). They interact with macrophages (which ingest foreign material), and also produce cytokines (interleukins) that induce the proliferation of B and T cells.

In addition, there are regulatory T cells (Treg cells) which are important in regulating cell-mediated immunity. The aim of these cells is to inhibit auto-reactive T cells and to quench T cell activation after successful elimination of a pathogen.

Natural killer (NK) cells and T cells are major components of tumor immunity, early observations of NK cells killing tumor cells being reported in the late 1960s. These cells form the active arm in the destruction of malignant cells. Current data supports an early participation of NK cells in innate immunity, while cytotoxic T lymphocytes (CTLs) seem to generate long-lasting effects on tumor growth. These two types of effector cells use the same lytic machinery to induce tumor cell death, but they have a distinctive set of antigen surface receptors to recognize target cells. While antigen-specific, MHC-restricted recognition of malignant cells is the key feature of T cells, the receptor repertoire in NK cells is different. Besides the well-known "killer-cell Ig-like" receptors (KIRs) and other receptors, NK cells express NCRs ("natural cytotoxicity receptors"). In this group of NCRs are the receptors NKp30, NKp44 and NKp46. The expression of NCRs is limited to NK cells whereas the cytotoxicity is related to the density of receptor expression on the cell surface, where the binding of a NCR leads to a strong activation of cytolysis.

Dendritic cells, i.e. professional antigen-presenting cells, play a critical role in innate and adaptive immune responses. In the development of spontaneous T-cell responses, the interaction between DC and other compartments of the immune system (T regs, T cells) is of central importance. The dendritic cells and other antigen presenting cells like macrophages "see" a foreign or aberrant antigen and therefore can induce a cascade of immune activation.

Helper (or TH) T cells: a helper (or TH) T cell is a T cell (a type of white blood cell) which has on its surface antigen receptors that can bind to fragments of antigens displayed by the class II MHC molecules-found on professional antigen-presenting cells (APCs). Once bound to an antigen, the TH cell proliferates and differentiates into activated TH cells and memory TH cells. Activated TH cells secrete cytokines, proteins or peptides that stimulate other lymphocytes; the most common is interleukin-2 (IL-2), which is a potent T cell growth factor. Activated, proliferating TH cells can differentiate into two major subtypes of cells, Th1 and Th2 cells. These subtypes are defined on the basis of specific cytokines produced. Th1 cells produce interferon-gamma and interleukin 12, while Th2 cells produce interleukin-4, interleukin-5 and interleukin-13, Memory TH cells are specific to the antigen they first encountered and can be called upon during the secondary immune response. Most TH cells have present on the cell surface the protein CD4, which is attracted to portions of the Class II MHC molecule. This affinity keeps the TH cell and the target cell bound closely together during antigen-specific activation. TH cells with CD4 surface protein are called CD4+ T cells.

Description of the In Vitro Method for Treatment Response Prediction in Cancer Patients Step a) of the Method At the end of step a) of the method according to the present invention, a quantification value is obtained for each of the at least one biological marker that is used.

Specific embodiments of step a) include:

quantifying one or more biological markers by immunochemical methods, which encompass quantification of one or more protein markers of interest by in situ immunohistochemical methods on complete tumor sections (whole slide analysis) of a tumor tissue sample, for example using antibodies directed specifically against each of the said one or more protein markers. In certain embodiments, the resulting quantification values consist of the density of cells expressing each of the protein markers in the tumor tissue sample under analysis. Alternatively a novel method based on the simultaneous use of fluorescently labelled antibodies and conventional immunohistochemistry can be used to detect specific immune cell subsets on the same tissue slide.

Additionally or alternatively, step a) of the method of the present invention includes quantifying one or more biological markers by protein expression analysis, which encompasses quantification of one or more biomarkers (cytokines, chemokines, other proteins) of interest, for example by performing a multiplex analysis.

Thus, in certain embodiments of the method, step a) consists of quantifying, in a tumor tissue sample, the cells expressing a specific biological marker of the adaptive immune response. Generally a combination of at least two biological markers is assayed. In these embodiments of step a) of the method, the value obtained at the end of step a) consists of the number or the density of cells of the immune system, or cell subsets thereof, that are contained in the said tumor tissue sample (including spatial information like the precise localization, e.g. the invasive margin etc.) and that express one specific biological marker, for example among the combination of biological markers. In these embodiments, what is obtained at the end of step a) consists of the cell density values found for each biological marker included in the combination of markers. As used herein, the density of cells of interest may be expressed as the number of these cells of interest that are counted per one unit of surface area of tissue sample, e.g. as the number of these cells of interest that are counted per $mm^2$ of surface area of tissue sample. As used herein, the density of cells of interest may also be expressed as the number of these cells of interest per one volume unit of sample. As used herein, the density of cells of Interest may also consist of the percentage of a specific cell subset (e.g. CD3+ T cells) per total cells or total cell subpopulation (set at 100%). This can also be represented by a ratio (e.g. CD3:CD8 cells). The inventors believe that the high statistical relevance that they have found between (i) the quantification values of the biological markers of interest, and (ii) the treatment response of the cancer patient may be explained at least by:

A highly precise quantification method for each marker, like the numbering of marker-expressing cells per surface area of a tumor tissue slice on whole tissue sections; this includes the centre of the tumor and the invasive margin and the surrounding tissue. Statistical relevance is then based on a broad area, making robust statistical deductions possible.

In contrast to Tissue Microarrays (TMA), whole tissue sections are evaluated in the invented method. This allows robust quantification for an individualized patient. Halama et al. (2010), Anal Quant Cytol Histol.; 32:333-40, have shown that only a statistically robust approach incorporating the whole tissue section analysis can provide a basis for individualized predictions.

In certain other embodiments of the method, step a) consists of quantifying, in a tumor tissue sample, the precise amount or level of one or more marker proteins of the immune response (e.g. cytokines, chemokines or other proteins). Immunohistochemical analysis to precisely identify the tissue compositions (e.g. immune cell densities or immune cell subpopulations) can be performed beforehand to unambiguously identify the tissue analyzed (see FIG. 5). Generally, this assessment for a combination of at least one marker protein is performed. In these embodiments of step a) of the method, what is obtained at the end of step a) consists of the expression level values found for each marker protein(s) specifically produced by cells from the immune system or from the tumor itself, that is included in the combination of markers.

Alternatively, the said expression level may be expressed as any arbitrary unit that reflects the amount of the protein of interest that has been detected in the tissue sample. Alternatively, the value obtained at the end of step a) may consist of a concentration of protein(s) of interest that could be measured by various protein detection methods. Examples include well known technologies: ELISA, SELDI-TOF, FACS, bead conjugated multiplex measurements or Western blotting.

In certain embodiments of step a) of the invented prediction process, the biological marker(s) is (are) quantified separately in one, or more than one, tumor tissue sample from the cancer patient, selected from the group consisting of (a) a global primary tumor (as a whole), (b) a complete tissue section, containing the centre of the tumor as well as tissue directly surrounding the tumor (specifically named the "invasive margin" of the tumor) in conjunction with (i) lymphoid islets in proximity to the tumor, (ii) the lymph nodes located in proximity of the tumor, (iii) a tumor tissue sample collected prior surgery (for follow-up of patients after treatment for example), and a sample (iv) from a distant metastasis, also encompassing the metastatic lesion as well as the adjacent normal tissue (also termed the "invasive margin"). In these embodiments, the density value that is obtained, at the end of step a), for each of the tumor: tissue samples (a, b, i-iv), is compared, at step b) of the method, with the corresponding reference values previously determined for each of the tumor tissue samples (a, b, i-iv), respectively. Obtaining, at step a) of the method, more than one quantification value for each biological marker that is used allows a more accurate prediction of treatment response than when only one quantification value per biological marker is determined In other embodiments of the treatment response prediction method according to the invention, quantification values for more than one biological marker are obtained, at step a) of the method. In these embodiments, step b) is carried out by comparing, for each biological marker used, (i) the quantification value obtained at step a) for this biological marker with (ii) the predetermined reference value for the same biological marker.

In further embodiments of the treatment response prediction method according to the invention, step a) is performed by obtaining quantification values for more than one tumor tissue sample for a single biological marker and step a) is performed by obtaining quantification values for more than one biological markers, which quantification values are then compared, at step b), with the corresponding predetermined reference values.

In preferred embodiments of the in vitro treatment response prediction method of the invention, step a) is selected from the group consisting of:
1) quantifying at least one biological marker in a complete tumor tissue section by immunohistochemical or immunofluorescence detection,
2) quantifying the said at least one biological marker in the whole tumor tissue sample by protein quantification analysis.

According to a first specific embodiment of the in vitro treatment response prediction method of the invention, step 1) is performed by quantifying at least two distinct biological markers, separately both (i) in the centre of the tumor (CT) and (ii) in the invasive margin (IM).

According to a second specific embodiment of the in vitro treatment response prediction method of the invention, step 2) is performed by quantifying at least one, distinct biological markers in the whole tissue sample.

When, in the in vitro method of the invention, step a) consists of step a2), then step b) is performed by comparing (i) each quantification value obtained for each biological marker of the said combination of at least one distinct biological markers.

Step b) of the Method

In step b) of the method, for each biological marker used, the value which is obtained at the end of step a) is compared with a reference value for the same biological marker, and when required with reference values. Said reference value for the same biological marker is thus predetermined and is already known to be indicative of a reference value that is pertinent for discriminating between a low level and a high level of the immune response of a patient with cancer, for the said biological marker. Said predetermined reference value for said biological marker is correlated with a good response to treatment in a cancer patient, or conversely is correlated with failure to treatment in a cancer patient.

Embodiments for Predetermining a Reference Value

Each reference value for each biological marker may be predetermined by carrying out a method comprising the steps of:
a) providing at least one collection of tumor tissue samples selected from the group consisting of:
a) a collection of tumor tissue samples from cancer patients classified as, Tis, or T1, or T2, or T3 or T4 and N0, or N1, or N2, or N3 and M0 or M1, and with no early metastasis or with early metastasis, not having undergone anti-cancer treatment;

b) quantifying, for each tumor tissue sample comprised in a collection of tumor tissue samples provided at step a), the said biological marker, whereby a collection of quantification values for the said biological marker and for the said collection of tumor tissue samples is obtained and the corresponding clinical data on response to treatment and progression free survival under treatment are collected;
c) calculating, from the said collection of quantified values obtained at the end of step b), the mean quantification value for the said biological marker in association with the clinical data, whereby then a predetermined reference value for said biological marker that is correlated with a specific treatment response is obtained.

The "anti-cancer treatment" that is referred to in the definition of step a) above relates to any type of cancer therapy undergone by the cancer patients after collecting the tumor tissue samples, including radiotherapy, chemotherapy and immunotherapy, e.g. antibody treatment.

According to the method for obtaining predetermined reference values above, more than one predetermined reference value may be obtained for a single biological marker. For example, for a single biological marker, the method above allows the determination of at least two predetermined reference values for the same biological marker. Other ways of determining the reference value include the calculation of the value at the median of the data sets and is fully disclosed in the example. Known statistical models can be used to generate clear reference values for good response to treatment or worse response to treatment (e.g. ROC curve analysis etc.)

Alternatively to reference values used for comparison at step b) of the method, a "cut-off" value can be determined.

As it is disclosed above, the said method allows the setting of a single "cut-off" value permitting discrimination between bad and good treatment outcome (e.g. response or no response to treatment). Practically, as it is disclosed in the examples herein, high statistical significance values (e.g. low P values) are generally obtained for a range of successive arbitrary quantification values, and not only for a single arbitrary quantification value. This dynamic range of values can nevertheless be used in the prediction process. In certain embodiments, a cut-off value consisting of a range of quantification values for the considered biological marker, consists of a range of values centred on the quantification value for which the highest statistical significance value is found (e.g. generally the minimum P value which is found).

In certain preferred embodiments of the method for predetermining a cut-off value that is described above, the said biological marker consists of the density of cells expressing a specific protein marker in the tumor sample. Additionally, for a single quantified protein marker, cut-off values for at least two distinct biological markers may be determined, respectively (i) a first cut-off value determined for a first biological marker consisting of the density of cells expressing the said protein marker on the whole tissue section and (ii) a second cut-off value determined for a second biological marker consisting of the quantification of protein levels in a given region.

Combinations of quantifications for cell densities and protein levels can be combined as for each of the evaluated biomarkers a differential reference value is obtained. Binary combinations therefore will yield four different classes of predictions. Higher numbers of combinations therefore will produce certain patterns of cell densities and concomitant protein levels (cytokine and/or chemokine levels) that distinguish patients with a response to treatment from those who do not respond to treatment.

In certain preferred embodiments of the method for determining cut-off values above, the said information relating to the actual clinical outcome of the patients are selected from the group consisting of (i) the duration of the progression free survival under treatment and (ii) the response to treatment.

Indeed, for performing the predictive method according to the invention, the availability of a predetermined reference value for more than one biological marker is preferred. Thus, generally, at least one predetermined reference value is determined for a plurality of biological markers indicative of the status of the immune response in reaction to the cancer that are encompassed herein, by simply reiterating any one of the methods for obtaining predetermined reference values that are described above, for a plurality of biological markers.

In certain embodiments, the reference predetermined value consists of a "cut-off" value, as already disclosed above, which "cut-off" value consists of a statistical quantification value for the biological marker of interest that discriminates between bad and good treatment response.

Illustratively, for metastatic lesions of human colorectal cancer a scoring system was identified by whole tissue section immunohistochemical analysis. A scoring system was developed to differentiate between patients with high or low TIL densities and to separate patients who responded to chemotherapy from those who did not respond to chemotherapy. An independent set of patients ("validation set") was used to validate the scoring system with respect to response prediction. Recursive partitioning analyses by conditional inference trees of the observed TIL densities (CD3, CD8, Granzyme B) of the 22 metastatic lesions in the training set revealed the following prediction rule: patients having a CD3 cell count above 600 cells/mm$^2$ are predicted to respond to therapy (P<0.001). Since one non-responder was misclassified as responder the rule was extended using the patient's CD8 and Granzyme B data. The finally derived rule required a CD3 cell count above 600/mm$^2$ and either a CD8 density of higher than 200/mm$^2$ or a Granzyme B density of higher than 30/mm$^2$ to predict response to treatment correctly. The resulting scoring system has a range from 0 to 4, with patients with a score of 0-2 having no response to treatment and shorter periods of progression free survival. Patients with a score of 3 or 4 have a response to treatment as measured objectively with the RECIST criteria. Patients with a score of 4 had a higher progression free survival period than patients with a score of 3. Accordingly, the number of CD3-positive, CD8-positive and/or Granzyme B-positive cells can be translated into a scoring system. Specifically, a score of 0-2 translates into a number of CD3-positive cells below 600 cells/mm$^2$ and a number of CD8-positive cells below 200 cells/mm$^2$ and/or a number of Granzyme B-positive cells below 30 cells/mm$^2$. Hence, in an alternative aspect, the present invention provides a method for predicting whether a cancer patient is responsive to treatment with cancer therapy, preferably chemotherapy or immunotherapy, comprising determining in a tumor sample from said patient the number of cells which are CD3-positive and CD8-positive and/or Granzyme B-positive, wherein a score of 3 or 4 is indicative that said patient is responsive to cancer therapy, preferably chemotherapy or immunotherapy. Conversely, the present invention also provides a method for predicting whether a cancer patient is responsive to treatment with cancer therapy, preferably chemotherapy or immunotherapy, comprising determining in a tumor sample from said patient the number of cells which are CD3-positive and CD8-positive and/or Granzyme B-positive, wherein a score of 0-2 is indicative that said patient is not responsive to cancer therapy, preferably chemotherapy or immunotherapy and/or has shorter periods of progression free survival.

Consistent with the findings above, patients with a response to chemotherapy had higher levels of Fractalkine, RANTES, MIF and MIG in the underlying tumor tissue. Also of predictive power were specifically IL-1a, IL-8, IP-10, HGF and SCGF-b among others. Accordingly, any of the aforementioned proteins can substitute CD3, CD8 and/or Granzyme B as predictive marker in the methods and uses of the present invention.

For instance, in certain embodiments wherein the biological marker consists, of a protein level, like RANTES, and wherein at step b) of the prediction method a quantitative analysis of the RANTES level at the tumor site is carried out, the predetermined reference value may be adjusted to the cell density value as obtained in a step a). Including a percentage of specific cells (e.g. CD3+) per total cells or total cell subpopulation (set at 100%), that is associated with outcome. This combined or "corrected" evaluation will allow a more reliable estimation when the available tissue is limited.

The optimal cut-off values based on unsupervised clustering and recursive partitioning tests, for CD3, CD8 and Granzyme B cell densities in the invasive margin of liver metastases were 600/mm$^2$ for the CD3 cell density and either a CD8 density of higher than 200/mm$^2$ or a Granzyme B density of higher than 30/mm$^2$.

In the alternative, the present invention also provides a method for predicting whether a cancer patient is not responsive to treatment with cancer therapy, preferably chemotherapy or immunotherapy, comprising determining in a tumor sample from said patient the number of cells which are CD3-positive and CD8-positive and/or Granzyme B-positive, wherein a number of CD3-positive and CD8-positive and/or Granzyme B-positive cells, that is below a predetermined number of said cells, which is indicative for patients responding to chemotherapy, is indicative that said patient is not responsive to cancer therapy, preferably chemotherapy or immunotherapy. The preferred cut-off values based on unsupervised clustering and recursive partitioning tests, for CD3, CD8 and Granzyme B cell densities in the invasive margin of liver metastases are 600/mm$^2$ for the CD3 cell density and either a CD8 density of higher than 200/mm$^2$ or a Granzyme B density of higher than 30/mm$^2$. A marker combination associated with a bad response to treatment is a combination where VEGF, IL-8 are high (in concentration) and Interferon gamma, MIG, IP-10 and Fractalkine are low (in concentration).

Another predictor of treatment response is CCL2. In some embodiments of the invention a high concentration of CCL2 is a predictor for bad treatment responses.

Another predictor of treatment response is MIF. In some embodiments of the invention a high concentration of MIF is a predictor for good treatment responses (i.e. in the case of anti-MIF treatment), whereas in other embodiments it is a predictor for worse treatment response.

Another predictor of treatment response is IL-1ra. In some embodiments of the invention a high concentration of IL-1ra is a predictor for good treatment responses (i.e. in the case of macrophage activating treatment), whereas in other embodiments it is a predictor for worse treatment response. Combinations of MIF, IL-1ra and/or CCL2 are therefore indicative of treatment responses.

According to the embodiments above, a failure to respond to treatment is expected if the quantification value generated for the cell density quantification in step a) is less than the predetermined cut-off reference values or alternatively when the comparison is carried out with a quantification of protein levels and the resulting protein level is below the determined reference value. As a third option, both cell quantification and protein levels can be combined, giving rise to complex patterns of response prediction with composite results from either cell quantification or protein level measurements. Conversely, a response to cancer treatment is expected if the quantification values generated for the cell densities are higher than the predetermined cut-off reference value or the measured protein concentrations are higher than the predetermined cut-off reference value, when the comparison is carried out at step b) of the method.

To further elaborate on the protein concentration or protein level measurements, in embodiments wherein the biological marker consists of the level of a protein related to the immune response of the human body, the predetermined reference value may consist of the protein level that correlates with failure of treatment, e.g. progression of the malignant disease under therapy, short progression free survival time, etc., or in contrast may consist of the protein level that correlates with good treatment response, e.g. no (radiographic) tumor load or metastasis at all or long progression free interval under treatment. The protein level or protein concentration value may be expressed as any arbitrary unit.

Comparison(s) Performed at Step b)

As already specified, and as it is shown in the examples herein, step b) of the in vitro treatment response prediction method of the invention consists of comparing, for each biological marker tested, respectively: (a) the quantification value found at step a) for the said biological marker, dependent on the technology use either quantified cell densities on whole tissue sections, quantified protein concentrations or the combination of both technical approaches; and
(b) the corresponding reference value that is already predetermined for the said biological marker.

When two or more biological markers are quantified at step a), then step b) consists of two or more comparison steps of the kind defined above.

Complex combinations of the technologies used for step a) can be put together into a meta-score, i.e. a scoring system where the outcome of different measurements have a pre-defined weight. E.g. a cell density of >1000 CD3+ positive cells/mm$^2$ within the primary tumor AND a protein level of >30000 ng/ml of RANTES add up to a score of "3", which on a scale of 0-3 is the highest possible score and associated with treatment response (see also below).

Also, when one specific biological marker is quantified at step a) in various tumor locations, and especially separately both in the centre of the tumor and in the invasive margin or in the adjacent normal tissue, then step b) comprises for the said specific biological marker the same number of comparison steps than the number of tumor locations wherein the said specific biological marker is quantified. Especially for situations wherein a specific biological marker is quantified separately for the centre of the tumor, the invasive margin for the adjacent normal tissue in step a), then step b) comprises, for the said specific biological marker, all necessary comparison steps, respectively: comparing the quantification value obtained at step a) for the said biological marker in the centre of the tumor, with the predetermined reference value in the centre for the tumor for the said biological marker and a step between the quantification value obtained at step a) for the said biological marker in the invasive margin, with the predetermined reference value in the invasive margin for the said biological marker and a step between the quantification value obtained at step a) for the said biological marker in the adjacent normal tissue, with the predetermines reference value in the adjacent normal tissue for the said biological marker.

In step b) therefore, the same number of single comparison steps than the number of quantification values that are obtained at step a) are performed. It is also possible due to the lack of tissue to perform evaluations only on the available regions, e.g. the center of the tumor.

The said comparison step b), irrespective of whether step a) consists of step i) immunohistochemistry or the novel technology of combining immunofluorescence and conventional immunohistochemistry on the same slide or step ii) protein level analysis or iii) a combination of both methods as defined above, preferably also comprises the calculation of a statistical relevance of the plurality of marker quantification values measured at step a), after their comparison with the corresponding reference values, e.g. using a statistical method like P Log Rank test.

In another embodiment of the invention, the said comparison step b) may include a binary classification of the quantification values measured at step a), for each biological marker, and optionally also for each separate region of tumor tissue tested (i.e. centre of the tumor, invasive margin, adjacent normal tissue), in two groups, respectively: (i) a first group termed "High" when the quantification value for the said biological marker, optionally in the said region of (tumor) tissue, is higher than the predetermined corresponding reference value and (ii) a second group termed "Low" when the quantification value for the said biological marker, optionally in the said region of (tumor) tissue, is lower than the predetermined corresponding reference value. Deducing from this, if the result of the comparison step b) consists of exclusively of "High" values for each marker tested, then a favourable treatment response for the said cancer patient is determined. Conversely, if the result of the comparison step b) consists of exclusively "Low" values for each marker tested, then a failure to treatment for the said cancer patient is determined. Intermediate conclusions are determined for "heterogeneous" patients, wherein, in the comparison step b), "High" quantification values are found for one or more of the biological markers tested and "Low" quantification values are found for the remaining markers of the combination of biological markers tested as it is disclosed in the examples herein. For these "heterogeneous" patients the treatment to response has to be defined beforehand and can result in a scoring system.

The inventors have shown, that only large scale whole slide imaging can provide a solid basis for individualized patient predictions and is already published by Halama et al. 2009. Therefore also small patient cohorts are informative and provide a basis for reference value estimations and calculations. Predictions have to rely on the same whole slide analysis if they are intended for individual patients, allowing a reproducible and accurate discrimination between patients with good response to treatment and with no response to treatment.

Thus, in a most preferred embodiment of the in vitro method according to the invention, the predetermined reference value for each specific biological marker, and optionally the region within the (tumor) tissue, that is used at the comparison step b) is calculated on the basis of whole slide analysis for the said marker, and optionally the said marker in the said region of the (tumor) tissue type, that are previously measured in tumor tissue samples originating from an adequate population of cancer-bearing individuals. For protein level quantification the identification and analysis of regions within the (tumor) tissue depends on the histological evaluation, wherefore a precise morphological assessment of the tissue on whole slide basis is also necessary.

Most preferably in view of obtaining highly relevant predetermined reference values for each biological marker of interest, the said predetermined reference values consist of the mean value of a multitude of whole slide quantification values of the said marker measured on tissue samples originating from the same large number of cancer-bearing patients which had a specific clinical outcome, i.e. response to treatment or failure of treatment.

The high accuracy of the described method lies within the high precision and robust measurement of large areas of tissue, namely through whole slide quantification. The combination of immunofluorescence and conventional immunohistochemistry makes the technology even more attractive, as this approach saves tissue and increases the information value of a single slide.

Most preferably, for assessing accurate predetermined reference values, the said reference values are predetermined from at least 30 quantification values, for a specific biological marker, thus using tissue samples originating from at least 30 cancer-bearing patients that have a defined clinical outcome, e.g. response to or failure of treatment. In preferred embodiments, a predetermined reference value is obtained from at least 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 or more quantification values for a specific biological marker.

The technology of tissue microarray is not suitable for individual patient predictions and can therefore only be used in the determination of reference values on large patient cohorts but not for individual patient predictions. The size of the tissue surface area of typical tissue microarrays is much too small for a statistically robust analysis.

(Optional) Step c) of the Method

As described above, the in vitro prediction method for the treatment outcome of cancer patients in this invention may further comprise a step c) wherein the prediction result per se is provided.

Depending on the biological marker(s) that are used, either:
(i) a good response to treatment for the cancer patient (with longer intervals of progression free survival under treatment) is determined, when the quantification value(s) obtained at step a) for a specific biological marker, or a specific combination of biological markers, is higher than, or lower than, respectively, the corresponding predetermined reference value(s); or
(ii) a failure of treatment for a cancer patient (or a shorter interval of progression free survival under treatment) is determined, when the quantification value(s) obtained at step a) for a specific biological marker, or a specific combination of biological markers, is higher than, or lower than, the said corresponding predetermined reference value(s);

In general, most of the biological markers used herein increase with an increased activation of the immune system in response against cancer. For instance, when the biological marker that is quantified at step a) consists of a protein specifically expressed by cells of the immune system, the quantification value of said marker increases with the level of the immune response against the cancer of the patient tested. Thus, when performing step b) of the response prediction method of the invention, a response to treatment is determined when the quantification value for a specific biological marker that is obtained at step a) is higher than the corresponding predetermined reference value, notably in embodiments wherein the predetermined reference value consists of a cut-off value. Conversely, a failure of treatment is determined when the quantification value obtained at step a) for a specific biological marker is lower than the corresponding predetermined reference value, notably in embodiments wherein the predetermined reference value consists of a cut-off value. However, there are molecules and cells involved in the process of immune activation (against cancer) that do hinder this activation. In this case, lower values of the said protein are favourable for the patient, as inhibition decreases. Thus, when performing step b) of the cancer treatment response prediction method of the invention, a good response to treatment is determined when the quantification value for a specific biological marker that is obtained at step a) is actually lower than the corresponding predetermined reference value, notably in embodiments wherein the predetermined reference value consists of a cut-off value. Conversely, a failure of treatment is determined when the quantification value obtained at step a) for a specific biological marker is higher than the corresponding predetermined reference value, notably in embodiments wherein the predetermined reference value consists of a cut-off value.

Given the above explanations, the impact and relation of the measured protein level or cell density has to be related to the clinical outcome, i.e. treatment response. Inhibitory cell populations or proteins are favourable for the patient when present in small numbers or lower amounts. Quantification or scoring system therefore has to incorporate this notion.

Specific embodiments of the methods used for performing step c) are fully detailed in the examples herein. For example, a patient with liver metastases of colorectal cancer has 800 CD3+ lymphocytes and 400 CD8+ cells/mm$^2$ at the invasive margin of the liver lesion. It is therefore predicted that this patient has a response to chemotherapy or immunotherapy. A similar patient with liver metastases of colorectal cancer has 105 CD3+ cells/mm$^2$ and 290 CD8+ cells/mm$^2$ and 39 Granzyme B+ cells/mm$^2$ at the invasive margin. This patient is therefore predicted not to have a response to chemotherapy. In a similar fashion, a patient with CXCL9 or CXCL10 of a concentration higher than 20 ng/ml tissue at the invasive margin is predicted to have a treatment response.

Combinations of biological Markers

As intended herein, a "biological marker" consists of any detectable, measurable or quantifiable, parameter that is indicative of the status of the immune response of the cancer patient in reaction to the tumor. A marker becomes a "biological marker" for the purpose of carrying out the prediction method of the invention when a statistical correlation is found between (i) an increase or a decrease of the quantified value for said marker and (ii) the response to treatment (and progression free survival under treatment) actually observed within patients. For calculating correlation values for each marker tested and thus determining the statistical relevance of said marker as a "biological marker" according to the invention, any one of the statistical method known may be used. Illustratively, statistical methods using Kaplan-Meier curves and/or univariate analysis using the log-rank-test and/or a Cox proportional-hazards model may be used, as it is shown in the examples herein. Any marker for which a P value of less than 0.05, and even preferably less than 0.001 (according to univariate and multivariate analysis) is determined, is viewed as a "biological marker" useable in the prediction method of the invention. Biological markers include the presence, or the number or density of or precise quantity, of cells or signalling molecules (cytokines, chemokines) from the immune system at the tumor site or in the adjacent tissue.

Biological markers also include the presence of, or the amount of proteins, which are specifically produced by cells from the immune system at the tumor site. Also biological markers are proteins that influence the immune system or modulate the immune system.

Biological markers thus include surface antigens that are specifically expressed by cells from the immune system, including e.g. B lymphocytes, T lymphocytes, monocytes/macrophages dendritic cells, NK cells, NKT cells, and NK-DC cells, fibroblasts, endothelial cells, etc. that are recruited within the tumor tissue or in the adjacent tissue, including within the invasive margin of the tumor and in the nearer lymph nodes.

Illustratively, surface antigens of interest used as biological markers include CD3, FOXP3, CD44, CD163, Granzyme B, NKp46, CD163, CD4, CD8 and CD45RO, that are expressed by NK cells, macrophages, T cells or T cell subsets.

For example, the expression of the CD3 antigen as a biological marker in the method according to the present invention, is indicative of the level of the immune response of the patient at the level of all T lymphocytes and NKT cells.

For example, the expression of the FOXP3 antigen as a biological marker in the method according to the present invention, is indicative of the level of the immune response of the patient at the level of regulatory T cells.

For example, the expression of the CD8 antigen as a biological marker in the method according to the present invention, is indicative of the level of the immune response of the patient at the level of cytotoxic T lymphocytes.

For example, the expression of the CD45RO antigen as a biological marker in the method according to the present invention, is indicative of the level of the immune response of the patient at the level of memory T lymphocytes or memory effector T lymphocytes.

Yet illustratively, proteins used as biological markers also include cytolytic proteins specifically produced by cells from the immune system, like perforin, granulysin and also granzyme-B.

The difference between "prognosis" and "treatment response" is a key concept in oncology. While patients can have a good prognosis, they still can have no treatment response and experience only side effects. Therefore it is essential to predict the prognosis or the overall survival of a patient and separately predict the treatment outcome and treatment response.

When performing the response prediction method of the invention with more than one biological marker, the number of distinct biological markers that are quantified at step a) are usually of less than 100 distinct markers, and in most embodiments of less than 50 distinct markers. They can however include any number of measurable biological markers.

Advantageously, high throughput screening of samples is sought, with as little as possible distinct biological markers. The higher the number of distinct biological markers that are quantified at step a) of the method, the more accurate the treatment response prediction will be.

The number of distinct biological markers necessary for obtaining an accurate and reliable response prediction, using the in vitro treatment response prediction method of the invention, may vary notably according to the type of technique for quantification which is performed at step a).

As it is shown in the examples herein, a reliable prediction may be obtained when quantifying a single biological marker at step a) of the method, as it is illustrated, for example, with quantification of CD3, CD8, CD45RO, GZM-B, RANTES, MIF and MIG biological markers.

Most preferably, when the in vitro response prediction method of the present invention is performed with biological markers consisting of the densities of cells expressing specific proteins, then step a) is performed through immunohistochemical techniques (i.e. conventional immunohistochemistry of the novel method described herein) and cell densities are measured (i) in the center of the tumor, (ii) in the invasive margin, (iii) in the adjacent normal tissue or (iii) separately in the centre of the tumor, in the invasive margin or in the adjacent normal tissue.

Most preferably, when the in vitro method for response prediction is performed with biological markers consisting of the concentration level of proteins of interest, then step a) is performed through protein analysis methods, like ELISA or multiplex bead-coupled protein measurements, starting from the whole tumor tissue that was initially collected from the cancer patient (and subsequent histological preparations), e.g. tumor tissue originating from a tumor resection during a surgical operation.

Thus, in preferred embodiments of the response prediction methods according to the present invention, the tumor tissue sample that is referred to in step a) is selected from the group consisting of (a) a (global) primary tumor (as a whole), (b) a complete tissue section, containing the centre of the tumor as well as tissue directly surrounding the tumor (specifically named the "invasive margin" of the tumor) in conjunction with (i) lymphoid islets in proximity to the tumor, (ii) the lymph nodes located at the proximity of the tumor, (iii) a tumor tissue sample collected prior surgery (for follow-up of patients after treatment for example), and a sample (iv) from a distant metastasis, also encompassing the metastatic lesion as well as the adjacent normal tissue Preferably, at least one biological marker is indicative of the status of the immune response of said patient against cancer, that is quantified at step a) and consists of at least one biological marker expressed by a cell from the immune system selected from the group consisting of B lymphocytes, T lymphocytes, monocytes/macrophages, dendritic cells, NK cells, NKT cells, and NK-DC cells.

Preferably, said at least one biological marker, that is quantified at step a), is selected from the group consisting of: (i) the number or the density of cells from the immune system contained in the tumor tissue sample and that express the said biological marker, generally a protein marker; and (ii) the level or concentration of a protein of interest in the tumor tissue sample or a given region of the (tumor) tissue sample.

In certain embodiments of the method, said at least one biological marker consists of the density of T lymphocytes present at the tumor site.

In certain other embodiments, said at least one biological marker consists of the quantification value of a protein expressed by cells from the immune system present at the tumor site as a whole or in a specific region within the (tumor) tissue sample.

In further embodiments of the method, said at least one biological marker consists of the quantification value of the concentration of a protein specifically expressed by cells from the immune system present at the tumor site.

A list of the preferred biological markers that may be used for carrying out the response prediction method by the above mentioned technologies is listed below.

Although the response prediction method according to the present invention has been tested for colorectal cancer, said method may be applied for all other cancer entities. Without wishing to be bound by any particular theory, the inventors believe that the response prediction methods of the invention may be successfully carried out for prediction the treatment outcome of any cancer patient that develops from a tumor to which cells from the immune system have access.

Deducing from the above statement, the response prediction method for cancer patients according to the present invention is potentially useful for determining the (clinical) treatment outcome of patients of a cancer selected from the group consisting of adrenal cortical cancer, anal cancer, bile duct cancer (e.g. peripheral cancer, distal bile duct cancer, intrahepatic bile duct cancer), bladder cancer, bone cancer (e.g. osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating, lobular carcinoma, lobular carcinoma in, situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adnocarcinroma, clear cell), esophagus cancer, gallbladder cancer (mucinous adenocarcinoma, small cell carcinoma), gastrointestinal carcinoid tumors (e.g. choriocarcinoma, chorioadenoma destruens), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer (e.g. melanoma, nonmelanoma skin cancer), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma). Primary cancers and metastases as well as cancers of unknown primary are included.

In further embodiments of the method, said at least one biological marker is selected from the group consisting of the following biological markers:

(i) Various Biological Markers

ICAM-2/CD102, 4-1BB/TNFRSF9, IFN-gamma R1, IFN-gamma R2, B7-1/CD80, IL-1 RI, IL-2 R alpha, BLAME/SLAMF8, IL-2 R beta, CCR3, CCR4, CCR5, CCR6, CCR7, CCR8, IL-7 R alpha, CCR9, CXCR1/IL-8 RA, CD2, CD3epsilon, CD3zeta, CD3gamma, CD4, CD4+/45RA−, IL-12 R beta 1, CD4+/45R0−, IL-12 R beta 2, CD4+/CD62L-ICD44, CD4+/CD62L+/CD441L-17, CD5, Integrin alpha 4/CD49d, CD6, Integrin alpha E/CD103, CD8, Integrin alpha M/CD11b, CD8+/45RA−, Integrin alpha X/CD11c, CD8+/45R0−, Integrin beta 21CD18, CD27/TNFRSF7, LAG-3, CD28, LAIR1, CD30/TNFRSF8, LAIR2, CD31/PECAM-1, CD40 Ligand/TNFSF5, NCAM-L1, CD43, NTB-A/SLAMF6, CD45, CD83, CD84/SLAMF5, RANK/TNFRSF11A, L-Selectin, CD229/SLAMF3, SIRP beta 1, CD69, SLAM, Common gamma Chain/IL-2 R gamma, CRACC/SLAMF7, CX3CRI, CXCR3, CXCR4, CXCR6, TNF RI/TNFRSF1A, TNF RII/TNFRSF1B, Fas/TNFRSF6, Fas Ligand/TNFSF6, TSLP, TSLP R, ICAM-11CD54, IL-2, IFN-gamma, IL4, IL-5, IL-10, IL-13, PD1, PD-L1, PD-L2, TIM3, (ii) Biological Markers of Th 1/Th2 Cells:

II-2R Common beta Chain, Common gamma Chain/IL-2 R gamma, IFN-gamma, IFN-gamma R1, IL-12, IFN-gamma R2, IL-12 R beta 1, IL-2, IL-12 R beta 2, IL-2 R alpha, IL-2 R beta, IL-24, TNF RI/TNFRSF1A, TNF RII/TNFRSF1B, IL-4 R, TNF-beta/TNFSF1B, (iii) Biological Markers of the Interferon Family:

IFN alpha, IFN beta, IFN-alpha/beta R1, IFN-alpha/beta R2, IFN-gamma R1, IFN-gamma R2, IFN-alpha A, IFN-alpha/beta R2, IFN-alpha B2, IFN-beta, IFN-alpha C, IFN-gamma, IFN-alpha D, IFN-alpha G, IFN-omega, IFN-alpha H2, (iv) Biological Markers of the Common Gamma Chain Receptor Family:

Common gamma Chain/IL-2 R gamma, IL-7 R alpha, IL-2, IL-9, IL-2 R alpha, IL-9 R, IL-2 R beta, IL-15, IL-15 R alpha, IL-21, IL-7, IL-21 R, IL-31, (v) Biological Markers of the CX3C Chemokines & Receptors:

CX3C Chemokine Ligands (IL-21, IL-22, IL-23, IL-31, IL-32, IL-33), CX3CL1/Fractalkine, CX3C Chemokine receptors, CX3CR1, (vi) Biological Markers of CXC Chemokines & Receptors, CXC Chemokine Ligands, CXCL13/BLC/BCA-1, CXCL11/I-TAC, CXCL14/BRAK, CXCL8/IL-8, CINC-1, CXCL10/IP-10/CRG-2, CINC-2, CINC-3, CXCL16, CXCL15/Lungkine, CXCL5/ENA, CXCL9/MIG, CXCL6/GCP-2, CXCL7/NAP-2, GRO, CXCL4/PF4, CXCL1/GRO alpha, CXCL12/SDF-1, CXCL2/GRO beta, Thymus Chemokine-1, CXCL3/GRO gamma, CXC Chemokine Receptors, CXCR6, CXCR3, CXCR1/IL-8 RA, CXCR4, CXCR2/IL-8 RB, CXCR5, (vii) Biological Markers of CC Chemokines & Receptors, CC Chemokine Ligands, CCL21/6Ckine, CCL12/MCP-5, CCL61C10, CCL22/MDC, CCL28, CCL3L1/MIP-1 alpha Isoform LD78 beta, CCL27/CTACK, CCL3/MIP-1 alpha, CCL24/Eotaxin-2, CCL4/MIP-1 beta, CCL26/Eotaxin-3, CCU 5/MIP-1 delta, CCL11/Eotaxin, CCL9/10/M1P-1 gamma, CCL14a/HCC-1, MIP-2, CCL14b/HCC-3, CCL19/MIP-3 beta, CCL16/HCC4, CCL20/MIP-3 alpha, CCL1/I-309/TCA-3, CCL23/MPIF-1, MCK-2, CCL18/PARC, CCL2/MCP-1, CCL5/RANTES, CCL8/MCP-2, CCL17/TARC, CCL7/MCP-3/MARC, CCL25/TECK, CCL13/MCP-4CC Chemokine Receptors, CCR1, CCR7, CCR2, CCR8, CCR3, CCR9, CCR4, D6, CCR5, HCR/CRAM-A/B, CCR6

(viii) Biological Markers of CC Chemokine Inhibitors

CCI, CC Viral Chemokine Homologs, MCV-type II, MIP-II, MIP-I, MIP-III (ix) Biological Markers of C Chemokines & Receptors The C (gamma) subfamily lacks the first and third cysteine residues. Lymphotactin (also known as SCM-1 alpha) and SCM-1 beta are currently the only two family members. Both have chemotactic activity for lymphocytes and NK cells.

C Chemokine Ligands, XCL1/Lymphotactin

C Chemokine Receptors, XCRI (x) Biological Markers of other Interleukins

IL-12, IL-12 R beta 1, IL-12 R beta 2, IL-27, IL-15, IL-31

In the present specification, the name of each of the various biological markers of interest refers to the internationally recognised name of the corresponding gene, as found in internationally recognised gene sequences and protein sequences databases, including in the database from the HUGO Gene Nomenclature Committee, that is available notably at the following Internet address: http://www.gene.ucl.ac.uk/nomenclature/index.html.

In the present specification, the name of each of the various biological markers of interest may also refer to the internationally recognised name of the corresponding gene, as found in the internationally recognised gene sequences and protein sequences database Genbank.

Through these internationally recognised sequence databases, the nucleic acid and the amino acid sequences corresponding to each of the biological marker of interest described herein may be retrieved by the one skilled in the art.

In yet further embodiments of the method, as already mentioned above, quantification values for a combination of biological markers are obtained at step a) of the cancer treatment response prediction method of the invention.

Thus, the cancer treatment response prediction method of the invention may be performed with a combination of biological markers. The number of biological markers used is only limited by the number of distinct biological markers of interest that are practically available at the time of carrying out the method. However, a too much high number of biological markers will significantly increase the duration of the method without simultaneously significantly improving the response determination.

Usually, in the embodiments wherein the response prediction method of the invention is performed with a combination of biological markers, not more than 50 distinct biological markers are quantified at step a). In most embodiments, a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50 distinct biological markers are quantified, However, as already mentioned previously in the present specification, the number of combined markers that are required for reaching a high statistical relevance (e.g. P lower than 0.001 will be depending from the kind of technique for quantifying the said combination of biological markers, at step a) of the in vitro treatment response prediction method.

In certain embodiments of the in vitro treatment response prediction method of the invention, wherein step a) is performed by quantifying biological markers with immunohistochemical techniques, then the use of a combination of a low number of markers may be sufficiently informative, specifically if the biological markers are separately quantified in the centre of the tumor, in the invasive margin or in adjacent normal tissue.

In still further embodiments of the method, the said at least one biological marker is selected from the group consisting of CD3, CD8, GZMB, CD45RO, GLNY, TBX21, IRF1, IFNG, CXCL9, CXCL10, CD4, CXCR3, CXCR6, IL-18, IL-18Rbeta, Fractalkine, IL-23, IL-31, IL-15, IL-7, MIG, Perforin, TCR[alpha][beta], TCR[gamma][delta], LAT, ZAP70, CD5 and CD2. These biological markers are preferably quantified, at step a) of the in vitro treatment response prediction method of the invention, by immunochemical methods, including in situ immunohistochemical methods. The quantification values may be expressed as the mean density of cells expressing a marker protein of interest contained per surface area of a tissue section from the tumor tissue sample Illustratively, a combination of 2, 3, 4, 5, 6, 7, 8, 9, 10, 11, 12, 13, 14, 15, 16, 17, 18, 19, 20, 21, 22, 23, 24, 25, 26, 27, or 28 distinct biological markers are quantified at step a), which biological markers are selected from the group consisting of CD3, CD8, GZMB, CD45RO, GLNY, TBX21, IRF1, IFNG, CXCL9, CXCL10, CD4, CXCR3, CXCR6, IL-18, IL-18Rbeta, Fractalkine, IL-23, IL-31, IL-15, IL-7, MIG, Perforin, TCR[alpha][beta], TCR[gamma][delta], LAT, ZAP70, CD5 and CD2 Quantification of this group of biological markers is preferably performed, at step a) of the in vitro treatment response prediction method of the invention, with immunohistochemical techniques.

Yet illustratively, a combination of 2 or more distinct biological markers which may be quantified at step a) of the in vitro treatment response prediction method of the invention may be selected 2 or more biological markers that are selected from the group consisting of CCR5, CR7, CD103, CD119, CD120a, CD120b, CD122, CD127, CD134, CD14, CD152, CD154, CD178, CD183, CD184, CD19, CD1a, CD210, CD25, CD26, CD27, CD28, CD3, CD32, CD4, CD44, CD45, CD45Ra, CD45Ro, CD47, CD49d, CD5, CD54, CD56, CD62L, CD69, CD7, CD8, CD80, CD83, CD86, CD95, CD97, CD98, CXCR6, GITR, HLA-DR, ICOS, IFN[gamma]RII, IL-18R[alpha], KIR-NKAT2, PD1, TCR[alpha][beta] and TGFRII. Quantification of this group of biological markers is preferably performed, at step a) of the in vitro treatment response prediction method of the invention, with immunohistochemical techniques.

Still further, combinations of at least two biological markers encompass combinations of two or more distinct biological markers selected from the group of biological comprising the following biological markers: T-box transcription factor 21 (T-bet), interferon regulatory factor 1 (IRF-1), IFN[gamma], CD3[zeta], CD8, granulysin (GLNY) and granzyme B (GZMB). Quantification of this group of biological markers is preferably performed, at step a) of the in vitro treatment response prediction method of the invention, with immunohistochemical techniques.

Illustratively, the combination of two biological markers may be selected from the group consisting of CD8A-TBX21, CD3Z-CD8A, CD3Z-TBX21, B7H3-TGFB1, IFNG-TBX21, CD4-CD8A, CD8A, IFNG, CD4-TBX21, CD3Z-CD4, CD4-TGFB1, CD8A-GLNY, IFNG-IRF1, GLNY-IFNG, IRF1-TBX21, IL8-PTGS2, GLNY-TBX21, CD3Z-GLNY, CD3Z-IFNG, GZMB-IFNG, GLNY-IRF1, IL10-TGFB1, CD8A-IL10, CD4-IL10, CD8A-GZMB, GZMB-TBX21, GD3Z-GZMB, CD4-tRFI, GNLY-GZMB, B7H3-IL10, CD4-GZMB, GZMB-IRF1, IL1[Omega]-TBX21, CD4-IFNG, B7H3-CD4, CD8A-TGFB1, CD3Z-IL10 and CD4-GNLY. Quantification of this group of biological markers is preferably performed, at step a) of the in vitro treatment response prediction method of the invention, with protein levels or concentration analysis techniques.

Other combinations of two biological markers that may be used, optionally with one or more distinct biological markers.

Further combinations of at least two markers that may be used, optionally with one or more distinct biological markers. Quantification of this group of biological markers is preferably performed, at step a) of the in vitro treatment response prediction method of the invention.

Still further, combinations of at least two biological markers encompass combinations of two or more distinct biological markers selected from the group of biological markers that are listed in Table 9 herein, comprising the following biological markers: 18s, ACE, ACTB, AGTR1, AGTR2, APC, APOA1, ARF1, AXIN1, BAX, BCL2, BCL2L1, CXCR5, BMP2, BRCA1, BTLA, C3, CASP3, CASp9, CCL1, CCL11, CCL13, CCL16, CCL17, CCL18, CCL19, CCL2, CCL20, CCL21, CCL22, CCL23, CCL24, CCL25, CCL26, CCL27, CCL28, CCL3, CCL5, CCL7, CCL8, CCNB1, CCND1, CCNE1, CCR1, CCR10, CCR2, CCR3, CCR4, CCR5, CCR6, CCR7, CCR8, CCR9, CCRL2, CD154, CD19, CD1a, CD2, CD226, CD244, PDCD1LG1, CD28, CD34, CD36, CD38, CD3E, CD3G, CD3Z, CD4, CD40LG, CD5, CD54, CD6, CD68, CD69, CLIP, CD80, CD83, SLAMF5, CD86, CDH1, CDH7, CDK2, CDK4, CDKN1A, CDKN1B, CDKN2A, CDKN2B, CEACAM1, COL4A5, CREBBP, CRLF2, CSF1, CSF2, CSF3, CTLA4, CTNN81, CTSC, CX3CL1, CX3CRI, CXCL1, CXCL10, CXCL11, CXCL12, CXCL13, CXCL14, CXCL16, CXCL2, CXCL3, CXCL5, CXCL6, CXCL9, CXCR3, CXCR4, CXCR6, CYP1A2, CYP7A1, DCC, DCN, DEFA6, DICER1, DKK1, Dok-1, Dok-2, DOK6, DVL1, E2F4, EBI3, ECE1, ECGF1, EDN1, EGF, EGFR, EIF4E, CD105, ENPEP, ERBB2, EREG, FCGR3A, CGR3B, FN1, FOXP3, FYN, FZD1, GAPD, GLI2, GNLY, GOLPH4, GRB2, GSK3B, GSTP1, GUSB, GZMA, GZMB, GZMH, GZMK, HLA-B, HLA-C, HLA-, MA, HLA-DMB, HLA-DOA, HLA-DOB, HLA-DPA1, HLA-DQA2, HLA-DRA, HLX1, HMOX1, HRAS, HSPB3, HUWE1, ICAM1, ICAM-2, ICOS, ID1, ifna1, ifna17, ifna2, ifna5, ifna6, ifna8, IFNAR1, IFNAR2, IFNG, IFNGR1, IFNGR2, IGF1, IHH, IKBKB, IL10, IL12A, IL12B, IL12RB1, IL12RB2, IL13, IL13RA2, IL15, IL15RA, IL17, IL17R, IL17RB, IL18, IL1A, IL1B, IL1R1, IL2, IL21, IL21R, IL23A, IL23R, IL24, IL27, IL2RA, IL2RB, IL2RG, IL3, IL31RA, IL4, IL4RA, IL5, IL6, IL7, IL7RA, IL8, CXCR1, CXCR2, IL9, IL9R, IRF1, ISGF3G, ITGA4, ITGA7, integrin, alpha E (antigen CD103, human mucosal lymphocyte, antigen 1; alpha polypeptide), Gene hCG33203, ITGB3, JAK2, JAK3, KLRB1, KLRC4, KLRF1, KLRG1, KRAS, LAG3, LAIR2, LEF1, LGALS9, LILRB3, LRP2, LTA, SLAMF3, MADCAM1, MADH3, MADH7, MAF, MAP2K1, MDM2, MICA, MICB, MKI67, MMP12, MMP9, MTA1, MTSS1, MYC, MYD88, MYH6, NCAM1, NFATC1, NKG7, NLK, NOS2A, P2×7, PDCD1, PECAM-, CXCL4, PGK1, PIAS1, PIAS2, PIAS3, PIAS4, PLAT, PML, PP1A, CXCL7, PPP2CA, PRF1, PROM1, PSMB5, PTCH, PTGS2, PTP4A3, PTPN6, PTPRC, RAB23, RAC/RHO, RAC2, RAF, RB1, RBL1, REN, Drosha, SELE, SELL, SELP, SERPINE1, SFRP1, SIRP beta 1, SKI, SLAMF1, SLAMF6, SLAMF7, SLAMF8, SMAD2, SMAD4, SMO, SMOH, SMURF1, SOCS1, SOCS2, SOCS3, SOCS4, SOCS5, SOCS6, SOCS7, SOD1, SOD2, SOD3, SOS1, SOX17, CD43, ST14, STAM, STAT1, STAT2, STAT3, STAT4, STAT5A, STAT5B, STATE, STK36, TAP1, TAP2, TBX21, TCF7, TERT, TFRC, TGFA, TGFB1, TGFBR1, TGFBR2, TIMP3, TLR1, TLRO1, TLR2, TLR3, TLR4, TLR5, TLR6, TLR7, TLR8, TLR9, TNF, TNFRSF10A, TNFRSF11A, TNFRSF18, TNFRSF1A, TNFRSF1B, OX-40, TNFRSF5, TNFRSF6, TNFRSF7, TNFRSF8, TNFRSF9, TNFSF10, TNFSF6, TOB1, TP53, TSLP, VCAM1, VEGF, WIF1, WNT1, WNT4, XCL1, XCR1, ZAP70 and ZIC2.

Yet further preferred combinations of at least two biological markers encompass combinations of two or more distinct biological markers selected from the group comprising the following biological markers: TNFRSF6B, CEACAM1, PDCD1LG1, CD8A, PTGS2, BIRC5, SELL, INDO, IRAK4, TNF, TNFRSF10A, MMP7, LILRB3, CD3Z, TNFRSF8, GAPD, CXCL10, EBAG9, IL8, STAT1, CXCR3, TGFB1, ICOS, CXCL9, CD97, IL18RAP, CXCR6, ART1, IRF1, B7H3, ACE, IL18R1, TBX21, IL18, PDCD1, IFNG, GNLY, GATA3, VEGF, GZMB, LAT, CD4, IRTA2, IL10, PD-1, PD-L1, PD-L2, TIM3, TNFSF4, THSD1 and PDCDILG2.

Any combination of at least two biological markers selected from the group of biological markers that are described in the present specification are herein encompassed by the invention.

In certain embodiments of the method, a combination of two biological markers is used at step a), that may be also termed herein a "set" of biological markers.

A specific set of biological markers, that may be quantified through protein levels or protein concentrations analysis techniques, consists of the set consisting of the following biological markers: PDCDILG1, VEGF, TNFRSF6B, IRF1, IL8RA and SELL. The said set of biological markers is of a high statistical relevance.

In view of the fact that it has been found for the first time by the present inventors that the measure of the level of the immune response or immune parameters of a cancer-bearing patient can be used as the sole measure for predicting the outcome of the treatment of the cancer disease, without any requirement of further data, the present invention relates in a second aspect to a method for predicting whether a cancer patient is responsive to treatment with cancer therapy, in particular chemotherapy, comprising determining in a tumor sample from said patient the number of cells which are CD3-positive and CD8-positive and/or Granzyme B-positive, wherein a number of CD3-positive and CD8-positive and/or Granzyme B-positive cells that is above a predetermined number of said cells, which is indicative for patients not responding to cancer therapy, in particular chemotherapy, is indicative that said patient is responsive to cancer therapy, in particular chemotherapy.

In the alternative, the present invention relates to a method for predicting whether a cancer patient is not responsive to treatment with cancer therapy, in particular chemotherapy, comprising determining in a tumor sample from said patient the number of cells which are CD3-positive and CD8-positive and/or Granzyme B-positive, wherein a number of CD3-positive and CD8-positive and/or Granzyme B-positive cells that is below or equal to a predetermined number of said cells, which is indicative for patients not responding to cancer therapy, in particular chemotherapy, is indicative that said patient is not responsive to cancer therapy, in particular chemotherapy.

When used herein, the term cancer therapy includes radiotherapy and chemotherapy, with chemotherapy being preferred.

In the context of the present invention the CD3-positive, CD8-positive and/or Granzyme B-positive cells are preferably immune cells, more preferably T cells including cytotoxic T cells, NK cells, NK T cells and/or NK-dendritic cells (NK-DCs).

As intended herein, the expression "prediction of treatment response or treatment outcome in a cancer patient" or "responsive to treatment" encompasses the treatment result prediction, in a patient wherein the occurrence of a cancer has already been diagnosed, including:
(i) the chances of treatment response, e.g. shrinkage of tumor burden;
(ii) the chances of long periods of progression free survival under treatment, including colorectal cancer.
Said term when used herein is equivalent to the term "susceptible to treatment" or "sensitive to treatment".

By "therapeutic effect" or "therapeutically effective" is meant that cancer therapy, in particular chemotherapy, may produce the therapeutic effect for which it is administered. Preferably, a therapeutic effect includes cellular or biological responses to a tumor. The response includes a complete response, a partial response, a stable disease (without progression or relapse), and/or a response with a later relapse of the patient from or as a result of the treatment with a cancer therapy, in particular chemotherapy. Preferably, cancer therapy, in particular chemotherapy may effect that tumor cells will undergo cell death, thereby, ameliorating and/or treating a tumor of a patient provided that said tumor cells are susceptible to chemotherapy. The means and methods of the present invention allow the determination of a patient's response to cancer therapy, in particular chemotherapy.

The therapeutic effect of the respective methods or method steps of the present invention may be detectable by all established methods and approaches which will indicate a therapeutic effect. It is, for example, envisaged that the therapeutic effect is detected by way of surgical resection or biopsy of an affected tissue/organ which is subsequently analyzed by way of, for example, immunohistochemical (IHC) or comparable immunological techniques. Alternatively it is also envisaged that tumor markers in the serum of the patient (if present) are detected in order to diagnose whether or not the therapeutic approach is effective. Additionally or alternatively, it is also possible to evaluate the general appearance of the respective patient (fitness, well-being, decrease of tumor-mediated ailment etc.) which will also aid the skilled practitioner to evaluate whether a therapeutic effect is already there. The skilled person is aware of numerous other ways which will enable him to observe a therapeutic effect of cancer therapy, in particular chemotherapy applied in the present invention.

Accordingly, the methods of the present invention also allow determining as to whether or not a therapy with a cancer therapy, in particular chemotherapy may be effective during the course of the therapy (i.e., the methods of the present invention allow monitoring the therapeutic effect of a cancer therapy, in particular chemotherapy). The likelihood that (a) cancer therapy is effective is preferably dependent on the number of CD3-, CD8-, and/or Granzyme B-positive cells as described herein.

Likewise, the methods of the present invention also allow determining as to whether or not a patient may respond favourably to a cancer therapy, in particular chemotherapy during the course of the therapy (i.e., the methods of the present invention allow monitoring the therapeutic effect of a cancer therapy, in particular chemotherapy).

The term "may respond favorably" when used in the context of the present application means that (a) tumor cell(s) and/or a subset of tumor cells, preferably tumor cells or a subset of tumor cells from a patient who is subject to cancer therapy is/are more likely to be susceptible to said cancer therapy. The likelihood that (a) tumor cell(s) and/or a subset of tumor cells (preferably obtained from a patient) may respond favorably is preferably dependent on the number of CD3-, CD8-, and/or Granzyme B-positive cells as described herein.

Similarly, the methods of the present invention also allow determining as to whether or not a cancer therapy, in particular chemotherapy, should be stopped and/or changed so as to apply a different therapy. Preferably, the decision as to whether a cancer therapy should be stopped and/or changed is made on the basis of the number of CD3-, CD8-, and/or Granzyme B-positive cells as described herein.

Accordingly, in connection with the methods of the present invention, it is envisaged that a sample of a patient who may be treated with a cancer therapy is to be obtained prior to the treatment, during the treatment and/or after the treatment. Preferably, the sample is obtained prior to the treatment in order to determine whether or not a patient may be susceptible to the treatment with a cancer therapy, in particular chemotherapy, whether or not a patient may respond favorably to the treatment with a cancer therapy, or whether or not a patient may benefit from the treatment with a cancer therapy, Summarizing, the methods of the present invention can equivalently be regarded as methods for predicting whether or not a patient may be susceptible to cancer therapy, whether or not a patient may respond favorably to cancer therapy, or whether or not a patient may benefit from cancer therapy.

The term "potentially" when used in the context of a therapeutic effect means that a cancer therapy, in particular chemotherapy—though cancer therapy is deemed to have a therapeutic effect based on the outcome of the methods of the present invention—does not necessarily have to be therapeutically effective. This is so because—self-explanatory as it is—the methods of the present invention cannot provide a 100% safe prediction whether or not a patient may be susceptible to cancer therapy, since individual factors such as age, body weight, general health, sex, diet, drug interaction and the like may have an influence as to whether or not a patient will be susceptible to cancer therapy.

However, if in a tumor sample from a patient the number of CD3-positive and CD8-positive and/or Granzyme B-positive cells is above a predetermined number of said cells, which is indicative for patients responding (or in some instances not responding) to cancer therapy, in particular chemotherapy, the likelihood that said patient is responsive to cancer therapy, preferably chemotherapy or immunotherapy as described herein, is more than 50%. Preferably the likelihood is more that 60%, 70%, 80% or 90%, more preferably more than 95%.

More specifically, if in a tumor sample from a patient the number of CD3-positive cells is at least about 600 cells/mm$^2$ and the number of CD8-positive cells is at least about 200 cells/mm$^2$ and/or the number of Granzyme B-positive cells is at least about 30 cells/mm$^2$, the likelihood that said patient is responsive to cancer therapy, preferably chemotherapy or immunotherapy as described herein, is more than 50% in comparison to a patient, a tumor sample from which does not have the indicated values of CD3-cells and CD8-cells and/or Granzyme B-cells (i.e., the tumor sample has lower values). Preferably the likelihood is more that 60%, 70%, 80% or 90%, more preferably more than 95%.

The term "tumor", as used herein, refers to all neoplastic cell growth and proliferation, whether malignant or benign, and all pre-cancerous and cancerous cells and tissues. Within the context of the present invention, the treatment of malignant tumors, i.e. cancers, is preferred.

Uses and methods of the invention can thus be used to treat tumors, including both solid and non-solid tumors. "Treat" or "treatment" as used herein, means to reduce, stabilize, or inhibit progression of a symptom, such as tumor size, number of metastases or other symptoms which are caused by/associated with the presence and/or progression of a tumor. A non-limiting exemplary list of cancerous diseases and tumors which can be treated with cancer therapy, in particular chemotherapy, is provided herein above in the context of the response prediction method. These tumors described herein may be metastatic or non-metastatic.

In the context of the present invention the term "cancer patient" (sometimes also denoted as patient subject or tumor patient) means a person suffering from cancer, thereby having a tumor, but also includes a person in risk of a tumor or a person suspected of having a tumor or a person diagnosed to suffer from a tumor. Preferably, said subject is a mammalian, such as a human, a horse, a camel, a dog, a cat, a pig, a cow, a goat or a fowl. A human subject is most preferred. The compositions, compounds, uses and methods of the present invention are thus applicable to both human therapy and veterinary applications.

As intended herein, a "tumor tissue sample" or, as also used equivalently herein, a "tumor sample" encompasses (a) a global primary tumor (as a whole), (b) a complete tissue section, containing the center of the tumor as well as tissue directly surrounding the tumor (specifically named the "invasive margin" of the tumor) in conjunction with (i) lymphoid islets in proximity to the tumor, (ii) the lymph nodes located in proximity of the tumor, (iii) a tumor tissue sample collected prior surgery (for follow-up of patients after treatment for example), and a sample (iv) from a distant metastasis, also encompassing the metastatic lesion as well as the adjacent normal tissue (also termed the "invasive margin").

A "tumor sample" (sometimes also denoted as "tissue sample") is preferably derived from a subject and may be obtained via biopsy such as needle biopsy, surgical biopsy, bone marrow biopsy etc. A tumor sample, thus, also includes a tumor, parts of a tumor, tumor cells derived from a tumor (including tumor cell lines which may be derived from a tumor and which are grown in cell culture), but also tumor cell lines as such, and cells and/or tissue which are/is derived from a subject and which are/is suspected of being tumorigenic or even cancerous or which are/is suspected of comprising tumorigenic or cancerous cells. A tumor tissue sample also encompasses pieces or slices of tissue that have been removed from the tumor and/or the surrounding tissue, including surgical tumor resection or the collection of a tissue sample by biopsy.

It is thus envisaged that the tumor sample may also comprise non-tumorigenic cells. For example tumor cells and/or (micro) metastases are frequently surrounded by healthy, i.e. non-tumorigenic tissue, i.e. the tumor cells could then form a subset of cells within the healthy tissue. A tumor sample thereby could comprise a subset of healthy (non-tumorigenic) cells and a subset of tumorigenic cells. As well, it is envisaged that a blood sample is analyzed for the concentration of certain cytokines and chemokines, whereby the blood sample not necessarily contains tumor cells. As well it is envisaged that a blood sample is analyzed for malignant or tumor cells. So the analysis of non-tumorigenic cells and tumorigenic cells can yield insight into the status of the immune status of the patient.

It is also envisaged that tumor samples may then be processed for further quantification of one or several biological markers, notably through histology or immunohistochemistry as outlined above methods and through methods of protein expression analysis, including proteomic analyses. It will be appreciated that this tumor tissue samples may be used in the prediction method of the present invention. In these embodiments, the level of expression of the biological marker can be assessed by assessing the amount (e.g. absolute amount or concentration) of the biological marker in a tumor tissue sample. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the biological marker in the sample.

The term "tumor site" refers to the tumor tissue itself as well as the tissue which is in close contact with the tumor tissue, including the invasive margin of the tumor and the regional lymph nodes that are close to the tumor tissue or to the invasive margin of the tumor. This tissue is usually termed "adjacent tissue".

"Determining the number of cells" as used herein in the context of the methods of the present invention refers to qualitatively and/or quantitatively, quantitatively being preferred, determining the number of cells. Any technique that is suitable to determine the number of cells can be applied, with whole slide imaging technology being preferred. The microscopically digitized slides resulting from whole slide imaging are subject to automatic image processing. The biological markers are thereby assessed automatically. Algorithms classify the sample of each patient towards their response to the treatment.

Preferably, the number of cells is determined as density of cells per square millimeter ($mm^2$). It is preferred that the number of cells is determined with immunohistochemistry and/or with immunofluorescence. Accordingly, it is a preferred embodiment of the present invention that the cells are detected by a labelled antibody or a labelled nucleic acid probe.

In some preferred embodiments of the second aspect, the method further comprises determining the level of at least one further biological marker being indicative of an immune response of the patient against the cancer, wherein a level that is above a predetermined level, which is indicative for patients not responding to chemotherapy, is indicative that said patient is responsive to cancer therapy, preferably chemotherapy or immunotherapy.

Biological markers (biomarkers) are described herein elsewhere and can thus be applied in said preferred embodiment.

Preferably, said biological marker is a protein which is indicative of an immune response, wherein a level of the protein that is above a predetermined level, which is indicative for patients not responding to cancer therapy, preferably chemotherapy or immunotherapy, is indicative that said patient is responsive to cancer therapy, preferably chemotherapy or immunotherapy.

In various preferred embodiments, said biological marker that is applied in said preferred embodiment of the method of the second aspect of the present invention is one or more selected from the group consisting of (a) immunological markers;
(b) biological markers of Th1/Th2/Th17 cells;
(c) biological markers of the Interferon family;
(d) biological markers of the Common gamma Chain Receptor Family;
(e) biological markers of the CX3C Chemokines and Receptors;
(f) biological markers of CXC Chemokines and Receptors;

(g) biological markers of CC Chemokines and Receptors;
(h) biological markers of CC Chemokines Inhibitors;
(i) biological markers of C Chemokines & Receptors
  Lymphotactin (also known as SCM-1 alpha) and SCM-1 beta, C Chemokine Ligands, XCLI/Lymphotactin, C Chemokine Receptors, XCR1;
(j) biological markers of other Interleukins;
(k) stem cell markers and molecules secreted by stem cells or leading to activation or mobilization of stem cells; and
(l) biological markers of growth factors, their receptors and correlated downstream-signalling molecules.

In a third aspect, the present invention provides one or more chemotherapeutic agents for use in the treatment of a cancer patient whose cancer is characterized by the infiltration of at least about 600 CD3-positive cells/mm$^2$ and at least about 300 CD8-positive cells/mm$^2$ and/or at least about 30 Granzyme B-positive cells/mm$^2$ comprising administering to said patient one or more therapeutically effective chemotherapeutic agents.

Similarly, in a fourth aspect the present invention provides a method of treating a cancer patient whose cancer is characterized by the infiltration of at least about 600 CD3-positive cells/mm$^2$ and at least about 300 CD8-positive cells/mm$^2$ and/or at least about 30 Granzyme B-positive cells/mm$^2$ comprising administering to said patient a therapeutically effective cancer therapy, preferably chemotherapy or immunotherapy.

Further, in a fifth aspect the present invention provides a method of stratifying cancer patients that are responsive to treatment with cancer therapy, preferably chemotherapy or immunotherapy, comprising determining the number of immune cells that infiltrate a tumor of a cancer patient, wherein a number of at least about 600 CD3-positive cells/mm$^2$ and at least about 300 CD8-positive cells/mm$^2$ and/or at least about 30 Granzyme B-positive cells/mm$^2$ indicates that the cancer patient is responsive to cancer therapy, preferably chemotherapy or immunotherapy.

Similarly, in the alternative, the present invention provides a method of stratifying cancer patients that are not responsive to treatment with cancer therapy, preferably chemotherapy or immunotherapy, comprising determining the number of immune cells that infiltrate a tumor of a cancer patient, wherein a number of less than about 600 CD3-positive cells/mm$^2$ and less than about 300 CD8-positive cells/mm$^2$ and/or less than about 30 Granzyme B-positive cells/mm$^2$ indicates that the cancer patient is not responsive to cancer therapy, preferably chemotherapy or immunotherapy. Any predefined cell number per surface area can be used as a threshold.

The term "stratifying" thus refers to sorting patients into those who may or may not benefit from cancer therapy.

In a sixth aspect, the present invention relates to a method of screening for a therapeutically effective chemotherapeutic agent for a cancer patient comprising the following steps:
(a) providing tumor cells from a tumor sample of said patient, wherein said tumor sample is characterized by the infiltration of at least about 600 CD3-positive cells/mm$^2$ and at least about 300 CD8-positive cells/mm$^2$ and/or at least about 30 Granzyme B-positive cells/mm$^2$;
(b) contacting the tumor cells with one or more chemotherapeutic agents; and
(c) evaluating whether said one or more chemotherapeutic agents affects the tumor cells.

Examples of specific chemotherapeutic agents that can be applied in methods, uses and kits of the present invention include: methotrexate; tamoxifen; fluorouracil; 5-fluorouracil; hydroxyurea; mercaptopurine; cisplatin; carboplatin; daunorubicin; doxorubicin; etoposide; vinblastine; vincristine; pacitaxel; thioguanine; idarubicin; dactinomycin; imatinib; gemcitabine; altretamine; asparaginase; bleomycin; capecitabine; carmustine; cladibrine; cyclophosphamine; cytarabine; decarazine; docetaxel; idarubicin; ifosfamide; irinotecan; fludarabine; mitosmycin; mitoxane; mitoxantrone; topotecan; vinorelbine; adriamycin; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; vorinostat; capecitabine; zoledronic acid; anastrozole; sunitinib; aprepitant and nelarabine, or a pharmaceutically acceptable salt thereof. In addition, the substances of the present invention can be used in combination with other agents that can be used to treat cancer such as acemannan; aclarubicin; aldesleukin; alitretinoin; amifostine; amrubicin; amsacrine; anagrelide; arglabin; arsenic trioxide; BAM 002 (Novelos); bicalutamide; broxuridine; celmoleukin; cetrorelix; cladribine; clotrimazole; DA 3030 (Dong-A); daclizumab; denileukin diftitox; deslorelin; dilazep; docosanol; doxercalciferol; doxifluridine; bromocriptine; cytarabine; HIT diclofenac; interferon alfa; tretinoin; edelfosine; edrecolomab; eflornithine; emitefur; epirubicin; epoetin beta; etoposide phosphate; exisulind; fadrozole; finasteride; fludarabine phosphate; formestane; fotemustine; gallium nitrate; gemtuzumab zogamicin; gimeracil/oteracil/tegafur combination; glycopine; goserelin; heptaplatin; human chorionic gonadotropin; human fetal alpha fetoprotein; ibandronic acid; interferon alfa; interferon alfa natural; interferon alfa-2; interferon alfa-2a; interferon alfa-2b; interferon alfa-NI; interferon alfa-n3; interferon alfacon-1; interferon alpha natural; interferon beta; interferon beta-1a; interferon beta-Ib; interferon gamma natural; interferon gamma-1a; interferon gamma-Ib; interleukin-1 beta; iobenguane; irsogladine; lanreotide; LC 9018 (Yakult); lefiunomide; lenograstim; lentinan sulfate; letrozole; leukocyte alpha interferon; leuprorelin; levamisole+fiuorouracil; liarozole; lobaplatin; lonidamine; lovastatin; masoprocol; melarsoprol; metoclopramide; mifepristone; miltefosine; mirimostim; mismatched double stranded RNA; mitoguazone; mitolactol; mitoxantrone; molgramostim; nafarelin; naloxone+pentazocine; nartograstim; nedaplatin; nilutamide; noscapine; novel erythropoiesis stimulating protein; NSC 631570 octreotide; oprelvekin; osaterone; paclitaxel; pamidronic acid; peginterferon alfa-2b; pentosan polysulfate sodium; pentostatin; picibanil; pirarubicin; rabbit antithymocyte polyclonal antibody; polyethylene glycol interferon alfa-2a; porfimer sodium; raltitrexed; rasburicase; rhenium Re 186 etidronate; RJI retinamide; romurtide; samarium (153 Sm) lexidronam; sargramostim; sizofiran; sobuzoxane; sonermin; strontium-89 chloride; suramin; tasonermin; tazarotene; tegafur; temoporfm; teniposide; tetrachlorodecaoxide; thymalfasin; thyrotropin alfa; toremifene; tositumomab-iodine 131; treosulfan; tretinoin; trilostane; trimetrexate; triptorelin; tumor necrosis factor alpha natural; ubenimex; bladder cancer vaccine; Maruyama vaccine; melanoma lysate vaccine; valrubicin; verteporfin; virulizin; zinostatin stimalamer; abarelix; AE 941 (Aeterna); ambamustine; antisense oligonucleotide; bcl-2 (Genta); APC 8015 (Dendreon); dexaminoglutethimide; diaziquone; EL 532 (Elan); EM 800 (Endorecherche); eniluracil; etanidazole; fenretinide; filgrastim SDOI (Amgen); galocitabine; gastrin 17 immunogen; HLA- B7 gene therapy (Vical); granulocyte macrophage colony stimulating factor; histamine dihydrochloride; ibritumomab tiuxetan; ilomastat; IM 862 (Cytran); inter leukin-2; iproxifene; LDI 200 (Milkhaus); leridistim; lintuzumab; CA 125 monoclonal antibody (MAb) (Biomira); cancer MAb (Japan Pharmaceutical Development); HER-2 and Fc MAb (Medarex); idiotypic 105AD7 MAb (CRC Technology); idiotypic CEA MAb (Trilex); LYM-I-iodine 131 MAb (Techniclone); polymorphic epithelial mucin-yttrium 90 MAb (Antisoma); marimastat; menogaril; mitumomab; motexafin gadolinium; MX 6 (Galderma); nolatrexed; P 30 protein; pegvisomant; porfiromycin; prinomastat; RL 0903 (Shire); rubitecan; satraplatin; sodium phenylacetate; sparfosic acid; SRL 172 (SR Pharma); SU 5416 (SUGEN); TA 077 (Tanabe); tetrathiomolybdate; thaliblastine; thrombopoietin; tin ethyl etiopurpurin; tirapazamine; cancer vaccine (Biomira); melanoma vaccine (New York University); melanoma vaccine (Sloan Kettering Institute); melanoma oncolysate vaccine (New York Medical College); viral melanoma cell lysates vaccine (Royal Newcastle Hospital); glycoengineered antibodies or valspodar.

Once a patient was identified or stratified in accordance with the teaching of the present invention to be responsive to cancer therapy, in particular chemotherapy, one or more chemotherapeutic agents which are particularly suited for the treatment of colorectal cancer or rectum cancer can be selected from the group consisting of UFT, Capecitabine, CPT-II, Oxaliplatin, 5FU, 5FU continuous infusion, Paclitaxel, Docetaxel, Cyclophosphamide, Methotrexate, Doxorubicin, Navelbine (iv and oral), Epirubicin, Mitoxantrone, Raloxifen, Cisplatin, Mitomycin, Carboplatinum, Gemcitabine, Etoposide and Topotecan. These chemotherapeutics can be combined with an anti-EPCAM antibody or any other antibody.

In a seventh aspect, the present invention provides a pharmaceutical package comprising one or more chemotherapeutic agents, and (a) instructions and/or an imprint indicating that said one or more chemotherapeutic agents is to be used for the treatment of a patient who suffers from cancer, wherein a tumor of said patient is characterized by the infiltration of at least about 600 CD3-positive cells/mm$^2$ and at least about 300 CD8-positive cells/mm$^2$ and/or at least about 30 Granzyme B-positive cells/mm$^2$; and/or (b) instructions and/or an imprint indicting that said patient is to be stratified by the method as described herein; and/or (c) means to carry out a method as described in any one of the preceding claims.

The invention includes a kit for assessing the outcome of a treatment in individual cancer patients (e.g. in a sample such as a tumor tissue patient sample). The kit comprises a multitude of reagents, each of which is capable of binding with or detecting specifically a biological marker protein. Suitable reagents for binding with a marker protein include antibodies, antibody derivatives, antibody fragments, beads (e.g. polystyrol etc.) and the like.

Thus, a further object of this invention consists of a kit for the response prediction of treatment in a cancer in a patient, which kit comprises means for quantifying at least one biological marker indicative of the status of the immune response (either on a cellular level or through signaling molecules) of said patient against cancer.

The kit of the invention may optionally comprise additional components useful for performing the methods of the invention. By way of example, the kit may comprise fluids (e.g. buffers, reagents for visualizing antibody-antigen reactions, etc.) for binding an antibody with a protein with which it specifically binds, one or more sample compartments, an instructional material which describes performance of the prediction method of the invention, and the like.

In certain embodiments, a kit according to the invention comprises one or a combination or a set of antibodies, each kind of antibodies being directed specifically against one biological marker of the invention to predict the outcome of treatment in a cancer patient.

In one embodiment, said kit comprises a combination or a set of antibodies comprising at least two kind of antibodies, each kind of antibodies being selected from the group consisting of antibodies directed against one of the CD3, CD8, GZMB, CD45RO, FOXP3, CD163, CD44, NKp46, CD1a, GLNY, TBX21, IRF1, IFNG, CD20, CXCL9, CXCL10, CXCR3, CD4, CXCR3, CXCR6, IL-18, IL-18Rbeta, Fractalkine, IL-23, IL-31, IL-15, IL-7, MIG, Perforin, TCR[alpha][beta], TCR[gamma][delta], LAT, ZAP70, CD5, CD2 or other biological markers.

An antibody kit according to the invention may comprise 2 to any number of antibodies, each type of antibodies being directed specifically against one biological marker of the invention. For instance, an antibody kit according to the invention may comprise 2, 3, 4, 5, 6, 7, 8, 9, 10, 11, 12, 13, 14, 15, 16, 17, 18, 19 or more types of antibodies, each kind of antibodies being directed specifically against one biological marker as defined herein.

Various antibodies directed against biological markers according to the invention encompass antibodies directed against biological markers selected from the group consisting of CD3, CD8, GZMB, CD45RO, FOXP3, CD163, CD1a, NKp46, GLNY, TBX21, IRF1, IFNG, CXCL9, CXCL10, CD4, CD20, CXCR3, CXCR6, IL-18, IL-18Rbeta, Fractalkine, IL-23, IL-31, IL-15, IL-7, MIG, Perforin, TCR[alpha][beta], TCR[gamma][delta], LAT, ZAP70, CD5 and CD2.

Various antibodies directed against biological markers according to the invention encompass antibodies directed against biological markers selected from the group consisting of CCR5, CR7, CD103, CDC119, CD120a, CD120b, CD122, CD127, CD134, CD14, CD152, CD154, CD178, CD183, CD184, CD19, CD1a, CD210, CD20, CD25, CD26, CD27, CD28, CD3, CD32, CD4, CD44, CD45, CD45Ra, CD45Ro, CD47, CD49d, CD5, CD54, C056, CD62L, CD69, CD7, CD8, CD80, CD83, CD86, CD95, CD97, CD98, CXCR6, GITR, HLA-DR, ICOS, IFN[gamma]RII, IL-18R[alpha], KIR-NKAT2, PD1, TCR[alpha][beta] and TGFRII.

Biological markers detectable by specific antibodies may also be selected from the group of biological markers consisting of CD3, CD8, GZMB, CD45RO, FOXP3, ALDH1, CD1a, CD163, NKp46, GLNY, TBX21, IRF1, IFNG, CXCL9, CXCL10, CD4, CXCR3, CXCR6, IL-18, IL-18Rbeta, Fractalkine, IL-23, IL-31, IL-15, IL-7, MIG, Perforin, TCR[alpha][beta], TCR[gamma][delta], LAT, ZAP70, CD5, CD2, CD20.

In certain other embodiments, a kit according to the invention comprises one or a combination or a set of pair of ligands or specific soluble molecules binding with one or more of the biological marker(s), of the invention.

In certain other embodiments, a kit according to the invention comprises one or a combination or a set of pair of specifically labelled (i.e. fluorescently labelled) specific antibodies against the abovementioned targets.

Figure 1:
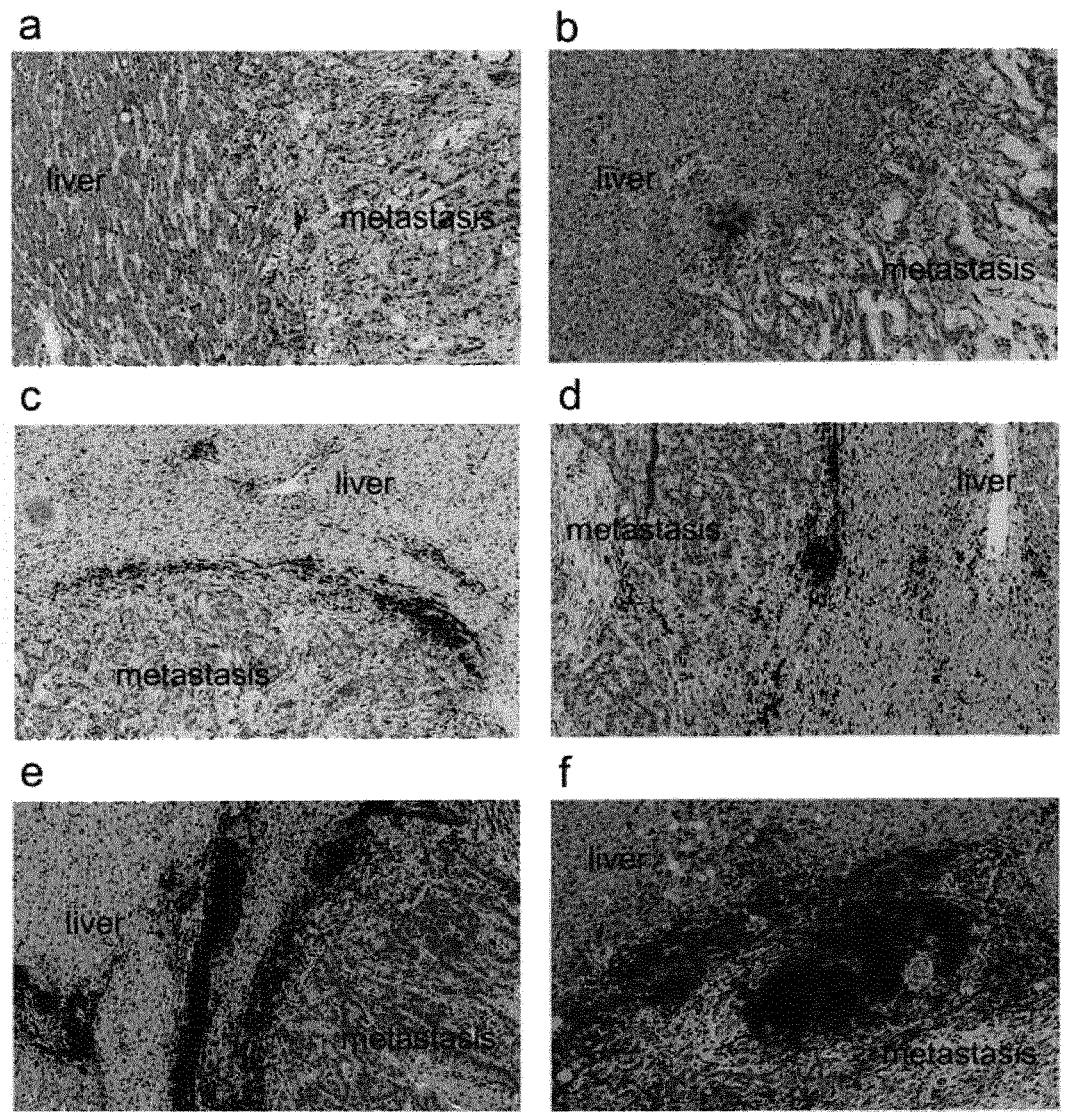
FIG. 1: Immunohistological images of liver metastases (digital magnification 10×), CD3 staining (dark red) and HE counterstaining. (a+b) showing the invasive margins from two different metastases from two different patients with a different density of infiltrating cells at the invasive margin (as represented by the 2+1+1 score), with a 2+1+1score of 0-2 (UP 2 and 4 months), (c+d) showing 2 metastases with a 2+1+1 score of 3 (UP 10 and 11 months), and (e+f) showing metastases from two different patients with a 2+1+1 score of 4 (UP 18 and 24 months).
Figure 2:
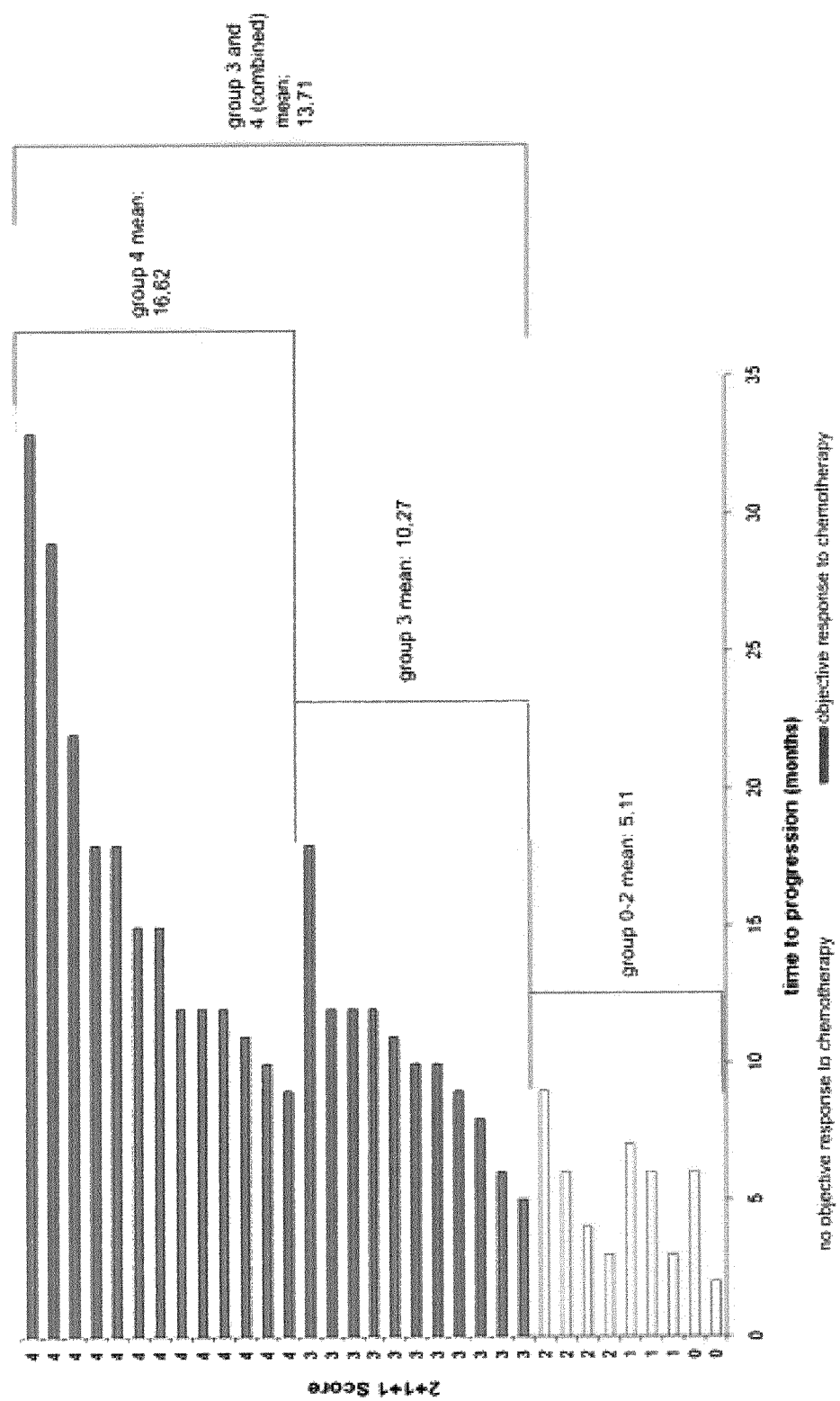
FIG. 2: Time to progression under chemotherapy (treatment) of patients according to the 2+1+1 scoring system (based on the analysis of the invasive margin of the liver metastases). Each horizontal bar represents a single patient, the length of the bar represents the individual time to progression (in months). The group with score 0-2 corresponds to the patients with no response to chemotherapy, average time to progression in months for each group is displayed (brackets show the respective group), differences between the groups were statistically significant.
Figure 3:
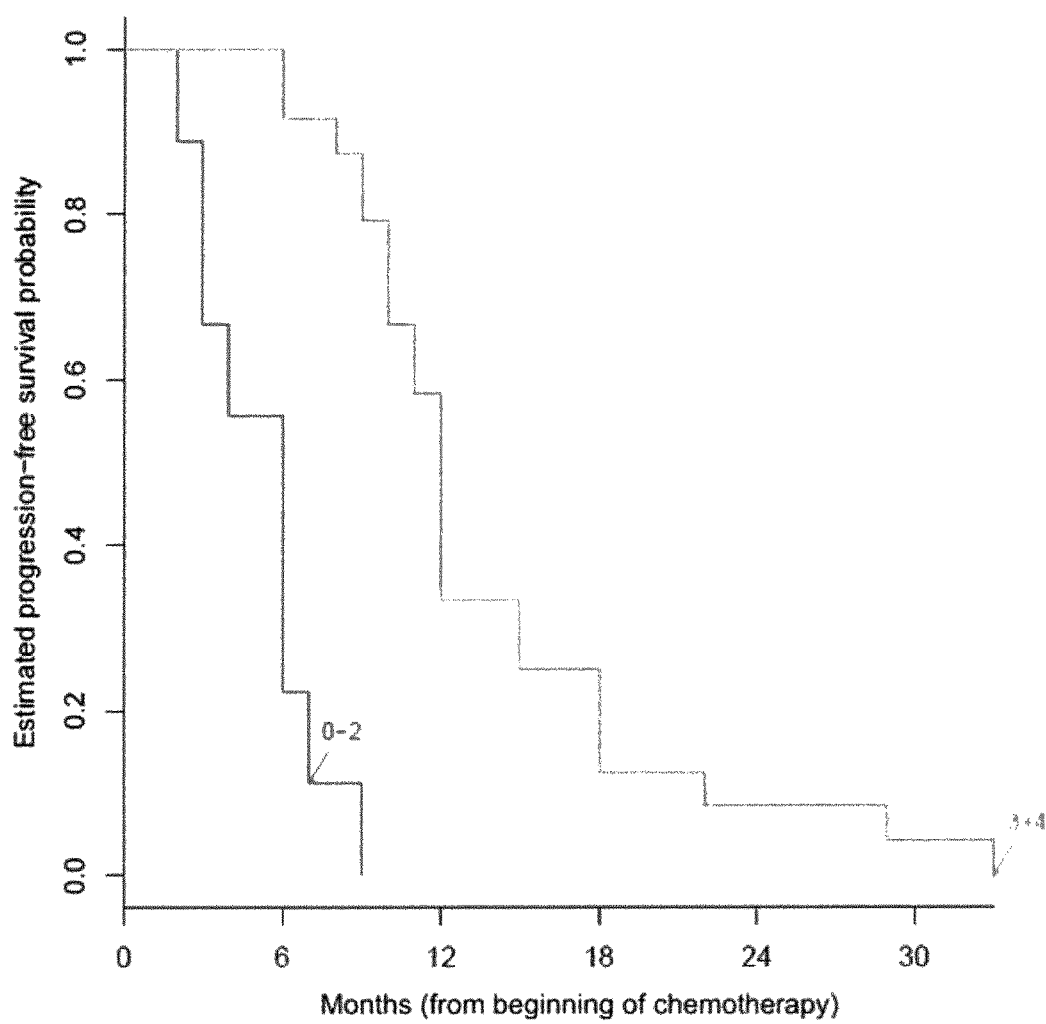
FIG. 3: Kaplan-Meier plot of estimated progression free survival probabilities across group 0-2 and group 3+4. Small arrows indicate corresponding groups.
Figure 4:
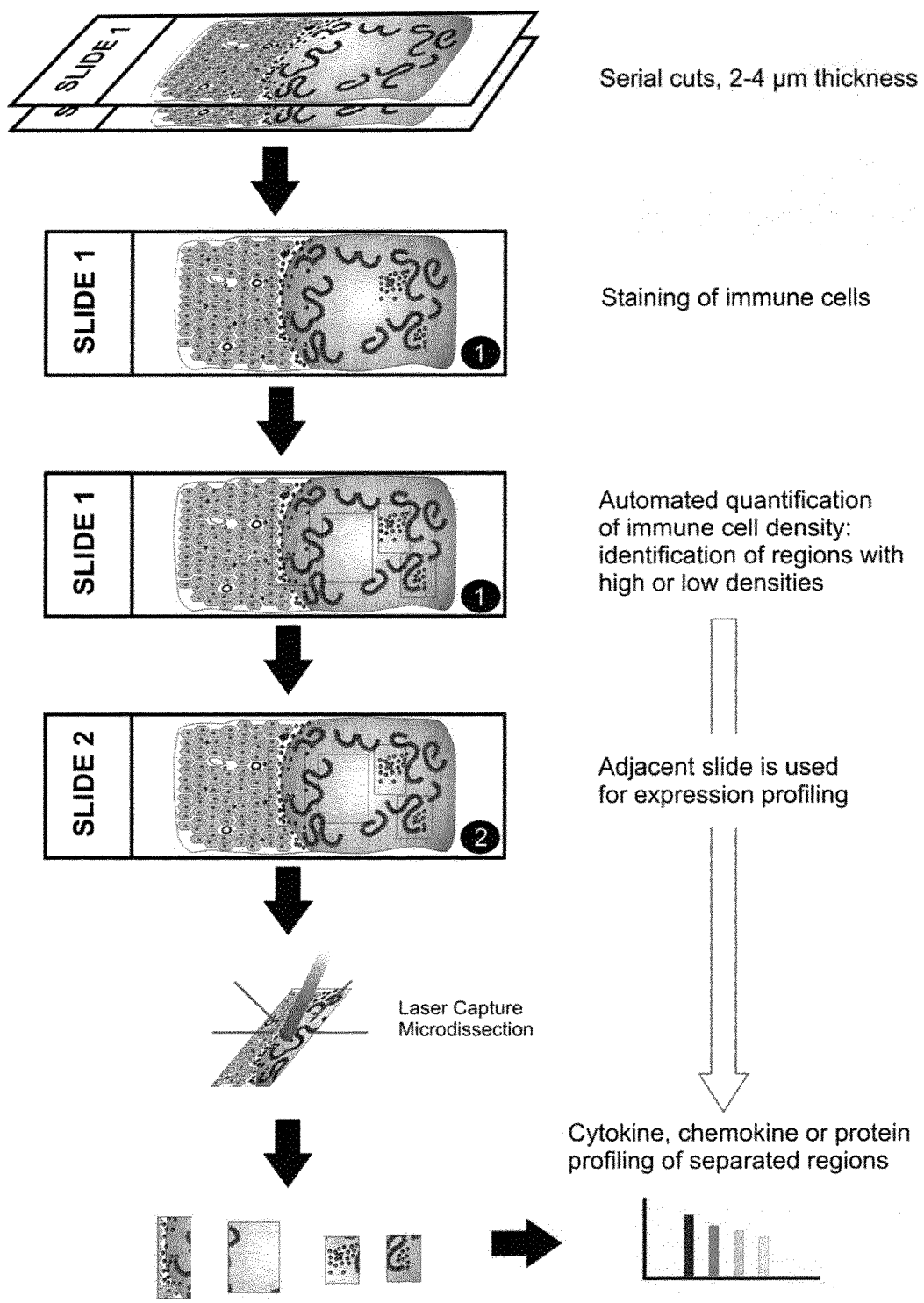
FIG. 4: Workflow for the precise quantification of immune cells and/or signaling molecules (protein quantification, e.g. cytokines and chemokines).
Figure 5:
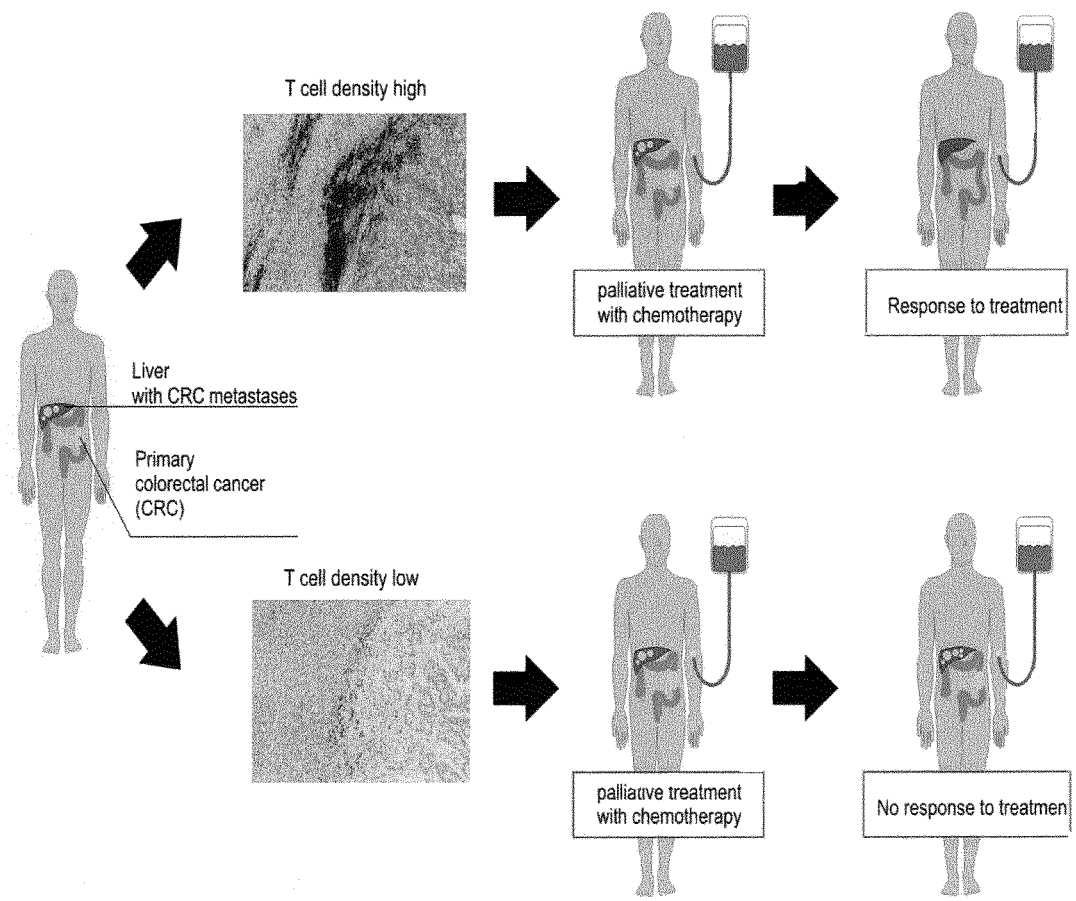
FIG. 5: Possible clinical workflow using the invention to identify patients that benefit from chemotherapy.
Figure 6:
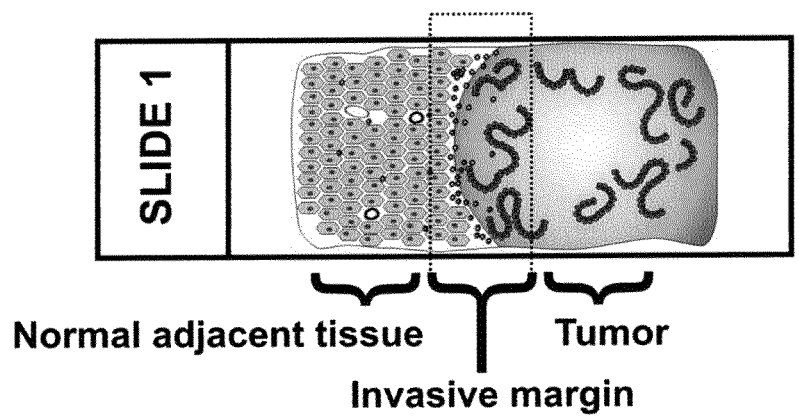
FIG. 6: Main regions of the tumor tissue and adjacent normal tissue (depicted in a section on a single slide).
Figure 7:
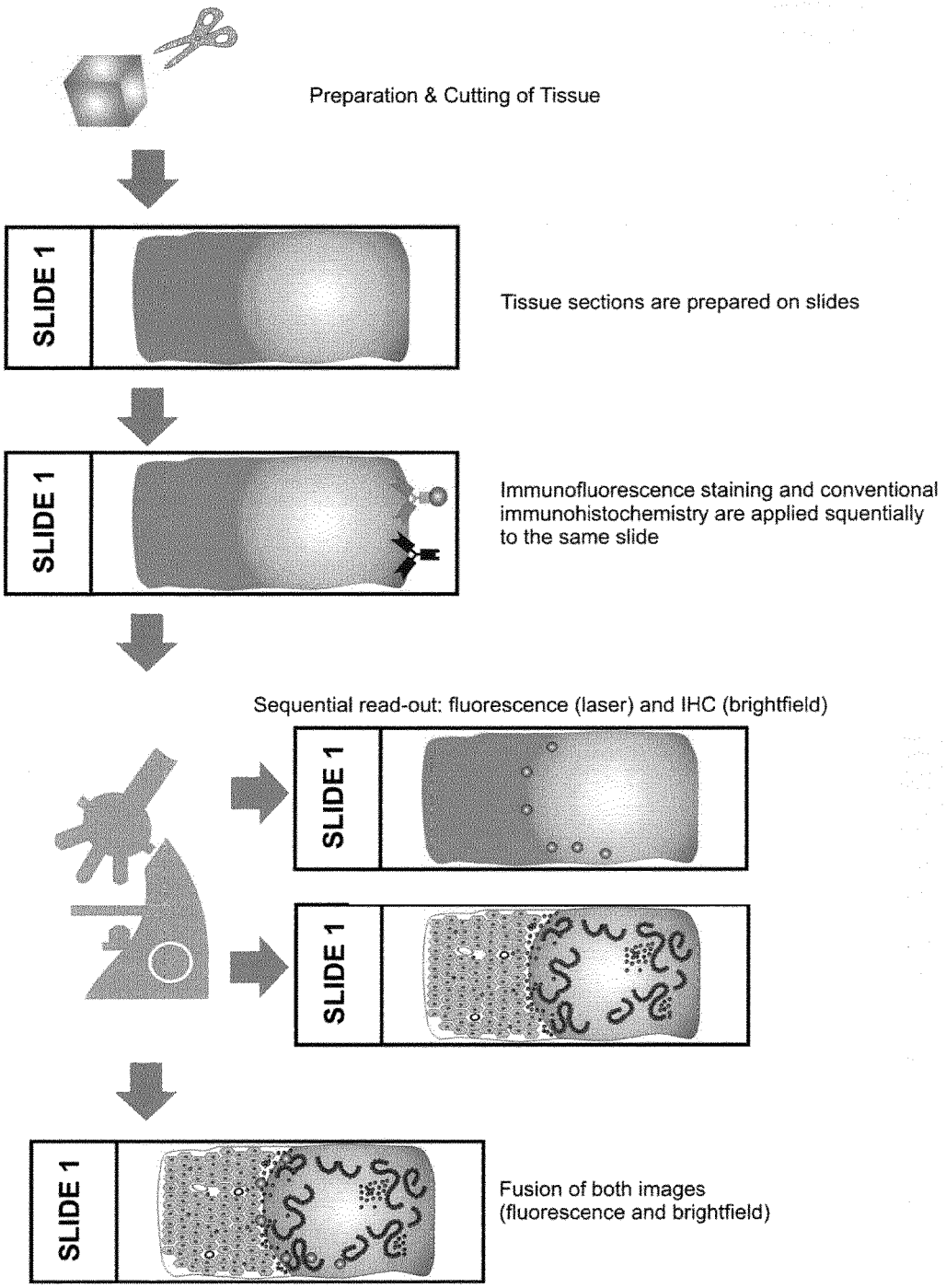
FIG. 7: Method of the present invention: combination of immunofluorescence and immunohistochemistry on the same slide (multiplex fluorescent IHC).

The invention claimed is:

1. An in vitro method for the prediction of treatment response of a cancer patient to cancer treatment comprising
   (a) obtaining a tumor sample from a patient, wherein the tumor sample is a tissue section of a solid tumor comprising the center of the tumor and tissue directly surrounding the tumor,
   (b) measuring in said tumor sample the density of cells which are CD3-positive by immunohistochemistry and immunofluorescence, wherein the measurement is conducted using whole slide imaging technology, and
   (c) determining measuring in said tumor sample the density of cells which are CD8-positive or Granzyme B-positive by immunohistochemistry and immunofluorescence, wherein the measurement is conducted using whole slide imaging technology,
   wherein the density of CD3-positive cells and the density of CD8-positive cells, or the density of CD3-positive cells and the density of Granzyme B-positive cells is measured across the complete tumor section, and wherein
   (i) a density of at least about 600 CD3-positive cells/mm$^2$ and a density of at least about 200 CD8-positive cells/mm$^2$, or
   (ii) a density of at least about 600 CD3-positive cells/mm$^2$ and a density of at least about 30 Granzyme B-positive cells/mm$^2$
   is indicative that said patient is responsive to cancer therapy.

2. The method of claim 1, wherein the cancer therapy is chemotherapy or immunotherapy.

3. The method of claim 1, wherein said positive cells are detected by a labeled antibody.

4. The method of claim 1, wherein said cancer is metastasizing cancer.

5. The method of claim 1, wherein said cancer is colorectal cancer.

6. The method of claim 1, wherein said tumor sample is from a primary tumor.

7. The method of claim 1, wherein said tumor sample is from a metastatic tumor.

8. The method of claim 1, wherein said tumor section further comprises
   (i) lymphoid islets in proximity of the tumor;
   (ii) lymph nodes located in proximity of the tumor; and/or
   (iii) adjacent normal tissue.

9. The method of claim 1, further comprising determining in said tumor sample from said patient the level of interferon gamma wherein a level of above 1000 ng/ml is indicative that said patient is responsive to cancer therapy.

10. The method of claim 1, further comprising determining in said tumor sample from said patient the ratio of interferon gamma to RANTES wherein a ratio higher than 1 is indicative that said patient is responsive to cancer therapy.

11. The method of claim 1, wherein said cancer is ovarian cancer, renal cell cancer, or melanoma.

12. A method of determining treatment efficacy in a cancer patient with a cancer comprising
   (a) obtaining a tumor sample from said patient, wherein the tumor sample is a tissue section of a solid tumor comprising the center of the tumor and tissue directly surrounding the tumor,
   (b) measuring in said tumor sample the density of cells which are CD3-positive by immunohistochemistry and immunofluorescence, wherein the measurement is conducted using whole slide imaging technology, and
   (c) measuring in said tumor sample the density of cells which are CD8-positive or Granzyme B-positive by immunohistochemistry and immunofluorescence, wherein the measurement is conducted using whole slide imaging technology,
   wherein the density of CD3-positive cells and the density of CD8-positive cells, or the density of CD3-positive cells and the density of Granzyme B-positive cells is measured across the complete tumor section, and wherein
   (i) a density of at least about 600 CD3-positive cells/mm$^2$ and a density of at least about 300 CD8-positive cells/mm$^2$, or
   (ii) a density of at least about 600 CD3-positive cells/mm$^2$ and a density of at least about 30 Granzyme B-positive cells/mm$^2$
   is indicative that the cancer therapy has efficacy in the cancer patient.

13. A method of treating a solid tumor in a patient, comprising
   (a) identifying a patient characterized by the infiltration of
      (i) at least about 600 CD3-positive cells/mm$^2$ and at least about 300 CD8-positive cells/mm$^2$ by whole slide imaging technology of an entire tumor tissue section comprising the tumor center and tissue directly surrounding the tumor, or
      (ii) at least about 600 CD3-positive cells/mm$^2$ and at least about 30 Granzyme B-positive cells/mm$^2$ by whole slide imaging technology of an entire tumor tissue section comprising the tumor center and tissue directly surrounding the tumor,
   and
   (b) administering to said patient a therapeutically effective chemotherapy.

* * * * *